US012678448B2

(12) United States Patent
Li et al.

(10) Patent No.: US 12,678,448 B2
(45) Date of Patent: Jul. 14, 2026

(54) POLYMERIC CARRIERS FOR DELIVERY OF THERAPEUTIC AGENTS

(71) Applicant: University of Pittsburgh—Of the Commonwealth System of Higher Education, Pittsburgh, PA (US)

(72) Inventors: Song Li, Mars, PA (US); Yixian Huang, Pittsburgh, PA (US); Haozhe Huang, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 697 days.

(21) Appl. No.: 18/014,867

(22) PCT Filed: Jul. 6, 2021

(86) PCT No.: PCT/US2021/040448
§ 371 (c)(1),
(2) Date: Jan. 6, 2023

(87) PCT Pub. No.: WO2022/010850
PCT Pub. Date: Jan. 13, 2022

(65) Prior Publication Data
US 2023/0293553 A1 Sep. 21, 2023

Related U.S. Application Data

(60) Provisional application No. 63/048,374, filed on Jul. 6, 2020.

(51) Int. Cl.
*A61K 31/606* (2006.01)
*A61K 9/107* (2006.01)
(Continued)

(52) U.S. Cl.
CPC .......... *A61K 31/606* (2013.01); *A61K 9/1075* (2013.01); *A61K 31/704* (2013.01); *A61K 47/34* (2013.01)

(58) Field of Classification Search
CPC .... A61K 31/606; A61K 9/1075; A61K 31/04; A61P 35/00
See application file for complete search history.

(56) References Cited

U.S. PATENT DOCUMENTS

| 6,562,330 B1 | 5/2003 | Straford |
| 6,676,971 B2 | 1/2004 | Goupil |
| (Continued) | | |

FOREIGN PATENT DOCUMENTS

| WO | WO2019204799 | 10/2019 |
| WO | WO2020077170 | 4/2020 |
| WO | WO2022010850 | 1/2022 |

OTHER PUBLICATIONS

Qiu, J.; Charleux, B.; Maty Jaszewski, K. Controlled/Living radical Polymerization in Aqueous Media: Homogeneous and Heterogeneous Systems; Prog. Polym. Sci. 2001, 26, 2083-2134.

(Continued)

*Primary Examiner* — Carlos A Azpuru
(74) *Attorney, Agent, or Firm* — BARTONY & ASSOCIATES, LLC

(57) ABSTRACT

A polymer includes a hydrophobic polymer backbone, a first plurality of pendant groups attached to the hydrophobic polymer backbone and including a first moiety including at least one group selected for ionic interaction with a second therapeutic agent, and a second plurality of pendant groups attached to the hydrophobic polymer backbone and including at least one hydrophilic polymer. The first moiety is attached via a labile bond and is released in vivo from the (Continued)

Hydrophilic polymer-targeting compound/group

Hydrophilic polymer

-drug residue for codelivery of a first therapeutic compound (e.g., COX Inhibitor)

ionic interaction

Second Therapeutic Compound polymer to provide a biologically or therapeutically active form of a first therapeutic compounds.

25 Claims, 26 Drawing Sheets

(51) Int. Cl.
    *A61K 31/704*     (2006.01)
    *A61K 47/34*     (2017.01)

(56)           References Cited

U.S. PATENT DOCUMENTS

| 8,318,816 | B2 * | 11/2012 | Hoffman | A61K 47/62 |
| | | | | 514/738 |
| 9,855,341 | B2 | 1/2018 | Li | |
| 10,172,795 | B2 | 1/2019 | Gao | |
| 10,376,591 | B2 | 8/2019 | Li | |
| 11,857,634 | B2 * | 1/2024 | Li | A61K 47/26 |
| 2011/0229572 | A1 * | 9/2011 | Lewis | A61P 35/00 |
| | | | | 424/487 |
| 2013/0244982 | A1 | 9/2013 | Dahan | |
| 2014/0030350 | A1 | 1/2014 | Ashrafi | |
| 2015/0150888 | A1 | 6/2015 | Resche-Rigon | |
| 2018/0214563 | A1 | 8/2018 | Li | |
| 2019/0038556 | A1 | 2/2019 | Gao | |

OTHER PUBLICATIONS

Matyjaszewski, K., Davis, T. P., Statistical, Gradient, Block, and Graft Copolymers by Controlled/Living Radical Polymerizations; Advances in Polymer Science; vol. 159; 2002, 1-168.
Matyjaszewski, K., Ed. Controlled Radical Polymerization; ACS: Washington, D. C., 1998; ACS Symposium Series 685.
Matyjaszewski, K., Controlled/Living Radical Polymerization. Progress in ATRP, NMP, and RAFT; ACS: Washington, D. C., 2000; ACS Symposium Series 768.
Matyjaszewski, K., Davis, T. P., Eds. Handbook of Radical Polymerization; Wiley: Hoboken, 2002, Chapter 8, 361-406.

* cited by examiner

Hydrophilic polymer-targeting compound/group

Hydrophilic polymer

-drug residue for codelivery of a first therapeutic compound (e.g., COX Inhibitor)

ionic interaction

Second Therapeutic Compound

-PEG-FA

-PEG

5-ASA

DOX

Fig. 4C 5-aminosalicylic acid sulfaslazine balsazide olsalazine aceclofenac diclofenac mefenamic acid tolfenamic acid doxrubicin pirarubicin carboplatin aclarubicin idrubicin nedplatin cisplatin amrubicin danobubicin oxiplatin epirubicin irinotecan lapatnib imatinib osimertinib sunitinib

Figure 4D:
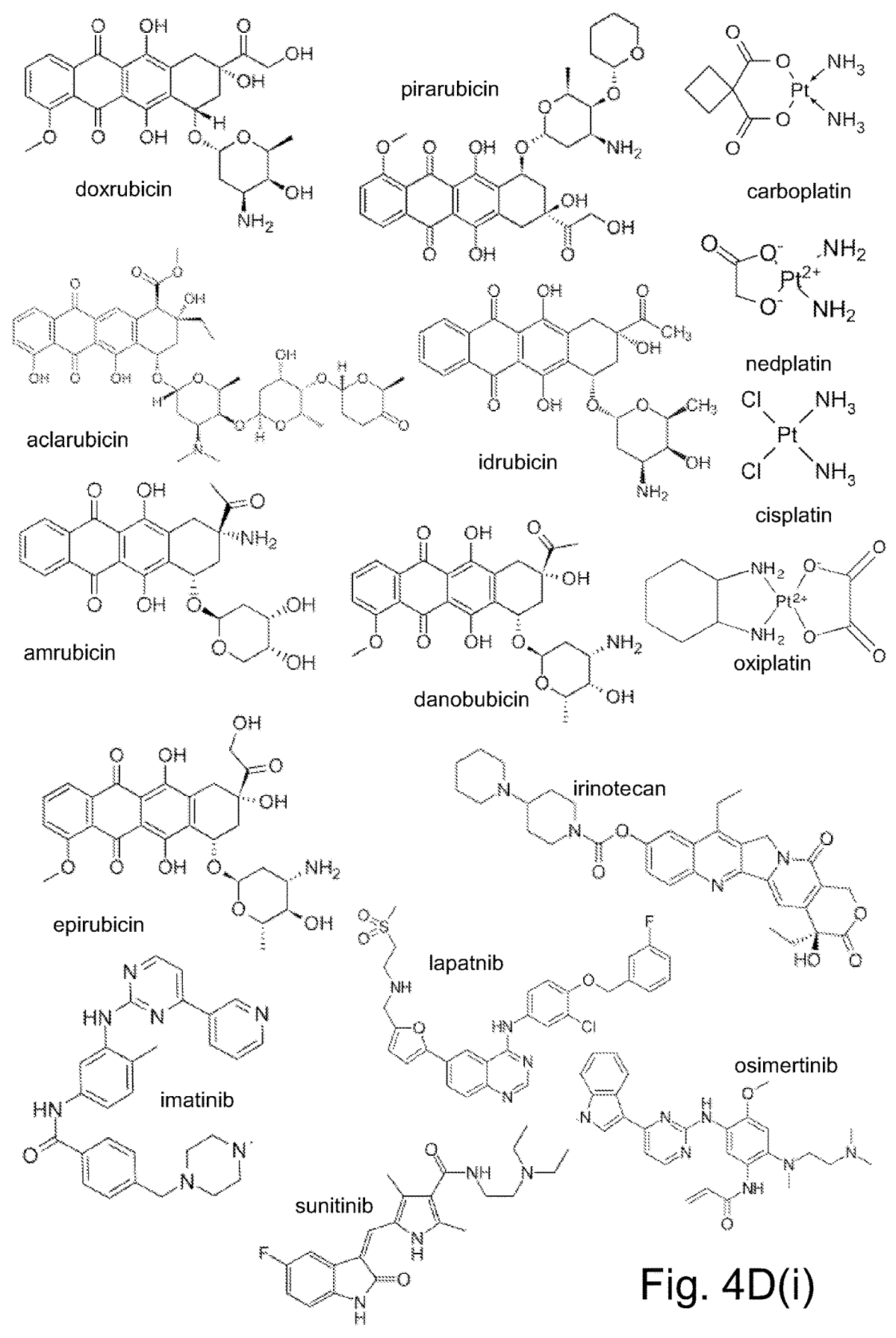

Fig. 4D(i)

ketoconazole olaparib rucaparib miconazole niraparib fluconazole talazoparib veliparib

Table 1

| Micelles | Mass Ratio (mg:mg) a | Size (nm) b | Zeta Potential (mV) b | DLC (%) c | DLE (%) d | Stability (d) e |
|---|---|---|---|---|---|---|
| PASA | | 197.6 | -10.99 | | | |
| PASA-DOX | 1:1 | 67.93 | -3.98 | 41.09 | 82.18 | >7 |
| PASA-DOX | 2:1 | 72.65 | -5.07 | 29.64 | 88.92 | >7 |
| PASA-DOX | 5:1 | 85.34 | -4.94 | 15.26 | 91.56 | >7 |
| PASA-DOX | 10:1 | 112.9 | -5.36 | 8.79 | 96.77 | >7 |
| PASA-DOX | 20:1 | 146.1 | -7.51 | 4.61 | 96.82 | >7 |
| FASA | | 197.5 | -11.47 | | | |
| FASA-DOX | 1:1 | 73.88 | -0.99 | 42.28 | 84.56 | >7 |
| FASA-DOX | 2:1 | 76.62 | -4.20 | 29.27 | 87.80 | >7 |
| FASA-DOX | 5:1 | 76.17 | -3.61 | 15.62 | 93.73 | >7 |
| FASA-DOX | 10:1 | 128.9 | -6.05 | 8.67 | 95.44 | >7 |
| FASA-DOX | 20:1 | 168.5 | -8.51 | 4.60 | 96.67 | >7 | a DOX concentration in micelles was kept at 0.5 mg/mL.
b Measured by dynamic light scattering particle sizer.
c DLC = drug loading capacity
d DLE = drug loading efficiency.
e Data mean there was no noticeable size change and visible precipitates during the
   follow-up period.

Fig. 8E

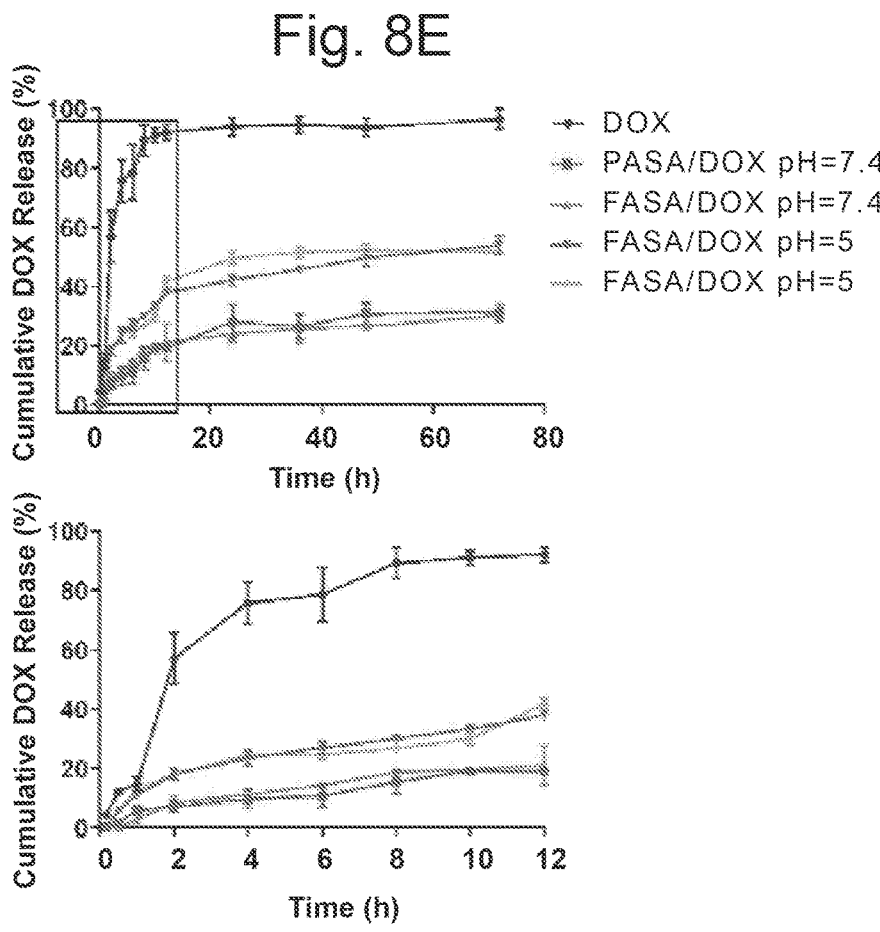

Fig. 8F

Table. 2. Size of PASA/Imatinib and FASA/Cisplatin micelles of various ratios.

| Micelles | Mass ratio (mg:mg) | Size (nm) |
|---|---|---|
| PASA:Imatinib | 1:1 | 35.57 |
| PASA:Imatinib | 2:1 | 39.53 |
| PASA:Imatinib | 5:1 | 47.57 |
| PASA:Imatinib | 10:1 | 52.13 |
| PASA:Cisplatin | 1:1 | 98.75 |
| PASA:Cisplatin | 2:1 | 134.7 |
| PASA:Cisplatin | 5:1 | 173.6 |

C10            Benzene ring

Hydrophilic chain

Benzene ring-C10

Fig. 17A

Sulfaslazine

DEAD, PPh₃

TFA

TEA

Fig. 17B

POLYMERIC CARRIERS FOR DELIVERY OF THERAPEUTIC AGENTS

CROSS-REFERENCE TO RELATED APPLICATIONS

This application is a US national phase filing of PCT International Patent Application No. PCT/US2021/040448, filed Jul. 6, 2021, which claims benefit of U.S. Provisional Patent Application Ser. No. 63/048,374, filed Jul. 6, 2020, the disclosure disclosures of which is are incorporated herein by reference.

GOVERNMENTAL INTEREST

This invention was made with government support under grant numbers CA223788 and CA219399 awarded by the National Institutes of Health. The government has certain rights in the invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Accumulating evidence indicates that chronic inflammation is a risk factor for various type of cancers. Prostaglandin E2 ($PGE_2$), a prostanoid lipid derived from cyclooxygenases, plays a predominant role in promoting inflammation and tumor progression by regulating downstream targets which control cell proliferation, angiogenesis and immunosuppression. Cyclooxygenase (COX)-1 and 2, critical for the production of $PGE_2$, are upregulated in various malignant tumors, including colorectal, breast, stomach, lung, and pancreatic cancers. Moreover, COX-2 overexpression is indicative of a poor outcome and recurrence, low survival rate, immune escape and resistance to cancer immunotherapy.

In contrast, absence of COX alters epidermal differentiation and attenuates the growth rate and incidence of papilloma formation. Moreover, genetic ablation of COX-2 in mouse melanoma, colorectal, breast and pancreatic cancer cells renders them susceptible to immune-dependent tumor growth control. Furthermore, conventional type 1 dendritic cells (cDC1) and natural killer (NK) cells, which are essential for antitumor immunity, have been found to assemble in the tumor microenvironment of COX-deficient tumors.

Various COX inhibitors have been developed and examined for their antitumor activity and the underlying mechanisms. For example, pharmacological inhibition of COX by Etodolac, a COX-2 selective inhibitor, has been shown to induce a dose dependent inhibition of endometrial cancer cells through G1 phase cell cycle arrest and inhibition of telomerase. Another COX inhibitor, Celecoxib significantly suppresses angiogenesis and tumor growth in CT26 tumor by extenuating $PGE_2$-mediated refractoriness to VEGF/VEGFR2 inhibition. In addition, Celecoxib enhances 5-Fluorouracil (5-FU) antitumor effects for esophageal squamous cell carcinoma indirectly by downregulating dihydropyrimidine dehydrogenase expression.

Despite the direct and indirect antitumor activity of various COX inhibitors, the underlying mechanisms remain poorly understood, particularly a role of tumor-derived COX in the actions of these inhibitors. Among those COX inhibitors, 5-aminosalicylic acid or 5-ASA is an FDA approved anti-inflammatory drug to treat inflammatory bowel disease, including ulcerative colitis and Crohn's disease. Many retrospective correlative studies have showed that the long-term use of 5-ASA can prevent the tumorigenesis. However, the direct anti-tumor activity and underlying mechanisms of 5-ASA is seldom reported. Only several studies use concentrations of 5-ASA significantly higher than the effective concentration required for inhibiting the COX activity. Few comparative studies were reported examining the antitumor activity of COX inhibitors on tumors with different expression levels of COX. More studies on the role of tumor-derived COX may assist in developing a more rational treatment of cancer.

Various small molecules, including COX inhibitors, have been developed as candidates for therapeutic treatments such as anti-cancer or anti-viral treatment of a patient. However, many drawbacks such as low water solubility, poor bioavailability and high toxic side effects limit clinical applications of such therapeutic agents or compounds. In, for example, cancer treatment, high doses of COX inhibitor are believed to be required for efficacy but often lead to significant toxicity such as gastrointestinal irritation and even bleeding.

Formulating small-molecule drugs into nano-sized micelles can increase the solubility and provide controllable drug delivery, which represents a promising strategy to enhance therapeutic efficacy and reduce systemic toxicity. It is known that the biodistribution profiles and tumor penetration of micelles can be tuned by optimizing the particle size. Decreasing nanoparticle size can increase circulation time and drug accumulation into tumors. However, smaller nanoparticles usually have lower drug payloads and loading efficiencies. Moreover, it may also be desirable to co-deliver a plurality of therapeutic agents or compounds via, for example, a carrier agent. Recently, micellular nanoparticles have been proposed for codelivery of a plurality of therapeutic agents.

SUMMARY

In one aspect, a polymer includes a hydrophobic polymer backbone (for example, formed via radical polymerization), a first plurality of pendant groups attached to the hydrophobic polymer backbone and including a first moiety comprising at least one group selected for ionic interaction with a second therapeutic agent, and a second plurality of pendant groups attached to the hydrophobic polymer backbone and including at least one hydrophilic polymer. The first moiety is attached via a labile bond and is released in vivo from the polymer to provide a biologically or therapeutically active form of a first therapeutic compound (for example, a COX inhibitor). In a number of embodiment, the first moiety is a residue of the first therapeutic compound (for example, a COX inhibitor) which may, for example, be formed by reacting the first therapeutic compound with a functional group of the polymer reactive with a functional group of the first therapeutic compound. A labile bond between the first moiety and the polymer may, for example, be formed to release the first therapeutic compound in vivo. The first moiety may, for example, be attached to the hydrophobic polymer backbone via a linking moiety or linker which interacts with the second therapeutic compound.

In a number of embodiments, the first moiety also includes one or more groups that may, for example, interact with the second therapeutic compound via hydrophobic interaction and/or via π-π bonding (for example, an aryl group such as a benzyl group). As set forth above, the first moiety further includes a group which is selected to interact ionically with at least one group of the second therapeutic agent. The group which interacts ionically with at least one group of the second therapeutic agent may, for example, be a carboxyl group (—COOH) or a pharmaceutically acceptable salt thereof. A generalized formula for a number of embodiments of compounds that may be reacted with precursors of the polymers hereof is set forth below.

In the above schematic structure, relevant functional groups are set forth. X is a functional group which may be reacted with a functional group on the polymer precursor. X may, for example, be —NH$_2$, —NH—, —OH, —CO$_2$H, or a group reactive to form an azo bond. The carboxyl, —CO$_2$H or —COOH group may be attached directly to the benzyl group or spaced therefrom The compound may further include one or more aryl groups such as a benzyl group to, for example, interact via hydrophobic interaction and/or π-π bonding and one or more carboxyl groups of the second therapeutic compound. In a number of embodiments, the compound that is reacted with the polymer precursor is the first therapeutic compound and the moiety is a residue of the first therapeutic compound.

In general, ionic interactions occur between two oppositely charged ions. Ions can also interact with a polar molecule (ion-dipole) or induce a dipolar character to a nonpolar molecule (ion-induced dipole). Certain groups selected for or capable of ionic interaction with other groups disassociate in aqueous solution (for example, in vivo) to become ionically charged and interact with other such groups of opposite charge. Other groups (for example, quaternary amines) may be inherently charged. The strength of ionic interactions depends, for example, upon the electrostatic charge density of the interacting ions, and the properties of the aqueous media (including dielectric constant and temperature).

In a number of embodiments, the hydrophobic polymer backbone is formed via radical polymerization of vinyl monomers. The hydrophobic polymer backbone may, for example, be formed via a free radical polymerization. The hydrophobic polymer backbone may, for example, be formed via a reversible-deactivation radical polymerization.

Bonds that are labile in vivo may, for example, include at least one of a reductive sensitive linkage or bond, a pH-sensitive linkage or bond, a ROS-sensitive linkage or bond, a hypoxia-sensitive linkage or bond (for example, an azo bond), or a protease-sensitive linkage or bond. The linking moiety that is labile in vivo may, for example, include at least one of an ester bond, an orthoester bond, a thioether-ester bond, an anhydride bond, an amide bond, a carbonate bond, a disulfide bond, a hydrazone bond, a cic-acotinyl bond, an acetal bond, a carboxydimethyl maleate bond, an imine bond, an oxime bond, a silyl ether bond, a ketal bond, a thioketal bond or a protease cleavable peptide.

In a number of embodiment, the polymer may further include a third plurality of pendant groups attached to the hydrophobic polymer backbone and including at least one targeting group to actively target a region of interest in vivo. The targeting group may, for example, target a tumor environment/microenvironment. In a number of embodiments, the targeting group includes a folate group, an anisamide, a peptide, or an antibody. In a number of embodiment, the targeting group includes a folate group.

In a number of embodiments, the labile bond of the moiety cleaves to release or provide a COX inhibitor such 5-aminosalycilic acid (5-ASA), acedofenac, diclofenac, mefenamic acid, tolfenamic acid, sulfasalazide, balsalazide, olsalazine or a derivative of such a compound which is active as a COX inhibitor. In a number of embodiments, the first therapeutic compound is 5-aminosalycilic acid or a derivative thereof which is active as a COX inhibitor. In a number of embodiments, COX inhibitors hereof include a carboxyl (—COOH) group as well as an amino group and/or a hydroxyl group.

In a number of embodiments, a plurality of the polymers hereof form a micelle having a diameter less than 100 nm, a diameter no greater than 80 nm, or a diameter no greater than 70 nm.

The second therapeutic compound may, for example, be an anticancer compound, an antiviral compound, an antibiotic compound, an antimycotic compound, an anti-rejection compound, an analgesic compound, an antioxidant compound, an immunomodulating compound, an antifungal compound, or an anti-inflammatory compound. In a number of embodiments, the second therapeutic compound may, for example, be an anticancer agent/compound (for example, a chemotherapeutic compound). In a number of embodiments, the second therapeutic compound is doxorubicin, pirarubicin, aclarubicin, idarubicin, amrubicin, daunorubicin, epirubicin, cisplatin, nedaplatin, oxaliplatin, carboplatin, irinotecan, imatinib, lapatinib, dabrafenib, trametinib, alpelisib, osimertinib, sunitinib, ketoconazole, miconazole, fluconazole, olaparib, rucaparib, niraparib, talazoparib, veliparib, MK-2206 a peptide (for example, an antimicrobial peptide), or an active derivative of such a compound.

In another aspect, a formulation hereof may, for example, includes a plurality of polymers including a hydrophobic polymer backbone, a first plurality of pendant groups attached to the hydrophobic polymer backbone and including a moiety attached to the hydrophobic polymer backbone via a bond which is labile in vivo to release a first therapeutic compound (for example, a COX inhibitor). The formulation further includes a second plurality of pendant groups attached to the hydrophobic polymer backbone and including at least one hydrophilic polymer and a second therapeutic compound, which is different from the first therapeutic compound. The moiety includes a group to ionically interact with a group of the second therapeutic compound. The first therapeutic compound may further include a group or groups capable of interacting via π-π bonding and/or hydrophobic interaction with the second therapeutic compound. The first moiety may, for example, be attached to the hydrophobic polymer backbone via a linking moiety or linker which interacts with the second therapeutic compound.

The first therapeutic compound and the second therapeutic compound may, for example, be small molecule compounds. Such small molecule therapeutic compounds may, for example, have a molecular weight below 1.5 kDa or below 1.0 kDa. The formulation may be further characterized as described above.

In a number of embodiments, each of the first therapeutic compound and the second therapeutic compound is a small molecule compound. Each of the first therapeutic compound and the second therapeutic compound has a molecular weight below 1.5 kDa or 1 kDa.

As described above, the hydrophobic polymer backbone may be formed via radical polymerization of vinyl monomers. The hydrophobic polymer backbone may, for example, be formed via a free radical polymerization. In a number of embodiments, the hydrophobic polymer backbone is formed via a reversible-deactivation radical polymerization.

As also described above, the bond which is labile in vivo includes at least one of a reductive sensitive linkage, a pH-sensitive linkage, a ROS-sensitive linkage, a hypoxia-sensitive linkage or bond, or a protease-sensitive linkage. In a number of embodiments, the bond which is labile in vivo includes at least one of an ester bond, an orthoester bond, a thioether-ester bond, an anhydride bond, an amide bond, a carbonate bond, a disulfide bond, a hydrazone bond, a cic-acotinyl bond, an acetal bond, a carboxydimethyl maleate bond, an imine bond, an oxime bond, a silyl ether bond, a ketal bond, a thioketal bond or a protease cleavable peptide.

The polymers may further include a third plurality of pendant groups attached to the hydrophobic polymer backbone and comprising at least one targeting group to target a region of interest in vivo. The targeting group may, for example, target a tumor environment. In a number of embodiments, the targeting group includes a folate group, an anisamide, a peptide, or an antibody. In another embodiment, the targeting group includes a folate group.

The first therapeutic compound may, for example, be 5-aminosalicylic acid, acedofenac, diclofenac, mefenamic acid, tolfenamic acid, sulfasalazine, balsalazide, olsalazine or a derivative thereof which is active as a COX inhibitor. In a number of embodiments, the first therapeutic compound is 5-aminosalicylic acid. The second therapeutic compound may, for example, be an anticancer compound/chemotherapeutic compound an antiviral compound, an antibiotic compound, an antimycotic compound, an anti-rejection compound, an analgesic compound, an antioxidant compound, an immunomodulating compound, an antifungal compound, or an anti-inflammatory compound. In a number of embodiments, the second therapeutic compound is an anti-cancer agent. In a number of embodiments, the second therapeutic compound is doxorubicin, pirarubicin, aclarubicin, idarubicin, amrubicin, daunorubicin, epirubicin, cisplatin, nedaplatin, oxaliplatin, carboplatin, irinotecan, imatinib, lapatinib, osimertinib, sunitinib, ketoconazole, miconazole, fluconazole, olaparib, rucaparib, niraparib, talazoparib, veliparib, MK-2206 or a peptide. In a number of embodiments, the second therapeutic compound includes an amino group to interact with the ionically interactive of the moiety. The second therapeutic compound may further include a group or groups to interact via π-π bonding and/or hydrophobic interaction.

In a number of embodiments, a plurality of the polymers hereof form a micelle (into which the second therapeutic compound may be loaded) having a diameter less than 100 nm, a diameter no greater than 80 nm, a diameter no greater than 70 nm. The micelle may, for example, have a loading capacity for the first therapeutic compound of at least 1-50% by weight, at least 4-50% by weight, at least 10-50% by weight or at least 20-50% by weight.

In another aspect, a formulation for delivery of a plurality of second therapeutic compounds in vivo includes a plurality of polymers (as described above) including a hydrophobic polymer backbone and a first plurality of pendant groups attached to the hydrophobic polymer backbone and including a moiety attached to the hydrophobic polymer backbone via a bond which is labile in vivo to release a first therapeutic compound (for example, a COX inhibitor), different from the second therapeutic compound. The formulation further includes a second plurality of pendant groups attached to the hydrophobic polymer backbone and including at least one hydrophilic polymer. The moiety of the first plurality of pendant groups includes a group to ionically interact with a group of the second therapeutic compound. The first moiety may, for example, be attached to the hydrophobic polymer backbone via a linking moiety or linker which interacts with the second therapeutic compound. The first therapeutic compound and the second therapeutic compound (as further characterized above) may, for example, be a small molecule compound. Such small molecule therapeutic compounds may, for example, have a molecular weight below 1.5 kDa or below 1.0 kDa. The plurality of polymers may, for example, form micelles.

In another aspect, a method of formulating a composition for delivery of a second therapeutic compound includes mixing a plurality of polymers (as described above) with a plurality of the second therapeutic compound. The polymers include a hydrophobic polymer backbone, a first plurality of pendant groups attached to the hydrophobic polymer backbone and including a moiety attached to the hydrophobic polymer backbone via a bond which is labile in vivo to release a first therapeutic compound (for example, a COX inhibitor), different from the second therapeutic compound. The first moiety may, for example, be attached to the hydrophobic polymer backbone via a linking moiety or linker which interacts with the second therapeutic compound. The polymers further include a second plurality of pendant groups attached to the hydrophobic polymer backbone and including at least one hydrophilic polymer with a plurality of the first compound. The polymers, the first therapeutic compound and the second compound may, for example, be further characterized as described above.

In a further aspect, a method of formulating a composition for delivery of a second therapeutic compound including mixing a plurality of polymers as described above with a plurality of the second therapeutic compounds. The plurality of polymers may form micelles. The second therapeutic compound may be loaded into such micelles. In a number of embodiments, the first therapeutic compound is a COX inhibitor.

In still a further aspect a method of delivering a first therapeutic compound and a second therapeutic compound includes administering a formulation as described above to administer a pharmaceutically effective amount of the first therapeutic compound and the second therapeutic compound. The formulations hereof may be administered by any conventional route of administration.

Systems, methods, and formulations/compositions hereof may, for example, be useful for the treatment of various cancers. COX inhibitors have been shown to have direct antitumor activity and promote antitumor immunity. However, these effects are often seen at concentrations that are significantly higher than the concentrations required to inhibit COX activity, which raises a safety concern, particularly in combination with a chemotherapeutic agent. The present systems, methods and formulations/compositions achieves effective COX inhibition at much lower concentrations, ameliorating these safety concerns.

Systems, methods, and formulations/compositions hereof may, for example, be useful for the immunomodulation of the tumor and tumor environment, which is important for successful anti-tumor therapy. Accumulating evidence indicates that chronic inflammation is a risk factor for various type of cancers. Prostaglandin E2 (PGE2), a prostanoid lipid derived from cyclooxygenases, plays a predominant role in promoting inflammation and tumor progression by regulating downstream targets which control cell proliferation, angiogenesis, and immunosuppression. Cyclooxygenase (COX)-1 and 2, critical for the production of PGE2, are upregulated in various malignant tumors, including colorectal, breast, stomach, lung, and pancreatic cancers. Moreover, COX-2 overexpression is indicative of a poor outcome and recurrence, low survival rate, immune escape, and resistance to cancer immunotherapy.

The present systems, methods, and compositions, along with the attributes and attendant advantages thereof, will best be appreciated and understood in view of the following detailed description taken in conjunction with the accompanying drawings.

BRIEF DESCRIPTION OF THE DRAWINGS

FIG. 4C illustrates formulas of representative first therapeutic compounds (COX inhibitors) for use herein.

FIG. 4D(i) illustrates formulas of representative second therapeutic compounds for user herein.

FIG. 4D(ii) illustrates formulas of further representative second therapeutic compounds for user herein.

FIG. 7A illustrates a synthetic scheme for polymers hereof (FASA) wherein the representative COX inhibitor X is 5-ASA, the hydrophilic polymer P is polyethylene glycol or PEG and the targeting compound/group Y is folic acid.

FIG. 7B illustrates a synthetic scheme for polymers hereof (PASA) wherein the representative COX inhibitor X is 5-ASA and the hydrophilic polymer P is polyethylene glycol.

FIG. 8E illustrates Table 1 setting forth size, zeta potential, DLC, DLE and stability of PASA/DOX and FASA/DOX micelles of various carrier/DOX ratios.

FIG. 8F illustrates cumulative DOX release profiles of PASA/DOX and FASA/DOX micelles under different pH with free DOX as control. (upper panel) 0-72 h and (bottom panel) 0 to 12 h, wherein DOX concentration was fixed at 0.5 mg/mL and values reported are the means±SEM for triplicate samples.

FIG. 14 illustrates Table 2 which sets forth size data of PASA/Imatinib and FASA/Cisplatin micelles of various ratios.

FIG. 15A illustrates an embodiment of a synthesis route of another PASA polymer hereof.

FIG. 17A illustrates an embodiment of a synthetic scheme hereof for the incorporation of the COX inhibitor diclofenac into a polymer hereof.

FIG. 17B illustrates an embodiment of a synthetic scheme hereof for the incorporation of the COX inhibitor sulfaslazine into a polymer hereof.

DESCRIPTION

Figure 1:
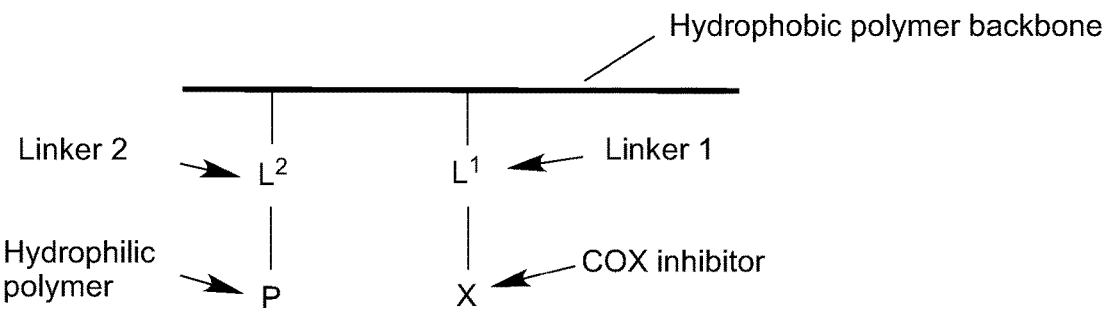
FIG. 1 illustrates schematically a representative embodiment of the generalized structure of an amphiphilic polymers hereof including moiety X which is releasable from the polymer as a first therapeutic compound (for example, a COX inhibitor) and a hydrophilic polymer P.

The present devices, systems, methods and compositions, along with the attributes and attendant advantages thereof, will best be appreciated and understood in view of the following description taken in conjunction with any accompanying drawings.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a compound" includes a plurality of such compounds and equivalents thereof known to those skilled in the art, and so forth, and reference to "the compound" is a reference to one or more such compounds and equivalents thereof known to those skilled in the art, and so forth. Recitation of ranges of values herein are merely intended to serve as a shorthand method of referring individually to each separate value falling within the range. Unless otherwise indicated herein, and each separate value as well as intermediate ranges are incorporated into the specification as if it were individually recited herein. All methods described herein can be performed in any suitable order unless otherwise indicated herein or otherwise clearly contraindicated by the text.

As used herein, the term "polymer" refers to a chemical compound that is made of a plurality of small molecules or monomers that are arranged in a repeating structure to form a larger molecule. Thus, a polymer is a compound having multiple repeat units (or monomer units) and includes the term "oligomer," which is a polymer that has only a few repeat units. The term "copolymer" refers to a polymer including two or more dissimilar repeat units (including terpolymers—comprising three dissimilar repeat units— etc.). Polymers may occur naturally or be formed syntheti- cally. The use of the term "polymer" encompasses homopo- lymers as well as copolymers. The term "copolymer" is used herein to include any polymer having two or more different monomers. Copolymers may, for example, include alternat- ing copolymers, periodic copolymers, statistical copoly- mers, random copolymers, block copolymers, graft copoly- mers etc. Examples of polymers include, for example, polyalkylene oxides.

As used herein, the term "pendant" refers to a group or moiety attached to a backbone chain of a long molecule such as a polymer as described above. Pendant group may be either (1) short chain or low molecular weight groups or (2) long chain or high molecular groups such as polymers. Pendant groups are sometime referred to as side groups. Long chain pendant groups or high molecular weight pen- dant groups are sometimes referred to as "pendant chains" or "side chains".

In a number of embodiments, systems, formulations, methods, and compositions hereof are provided for co- delivery of small molecule therapeutic agents or drugs. For example, a second therapeutic agent which is loaded into micelles formed from polymers hereof (for example, a chemotherapeutic or anticancer therapeutic agent or drug) may be delivered with a first therapeutic agent (for example, a COX inhibiting agent or drug) which is released from covalent, labile attached to the polymer as a pendant group.

Figure 2:
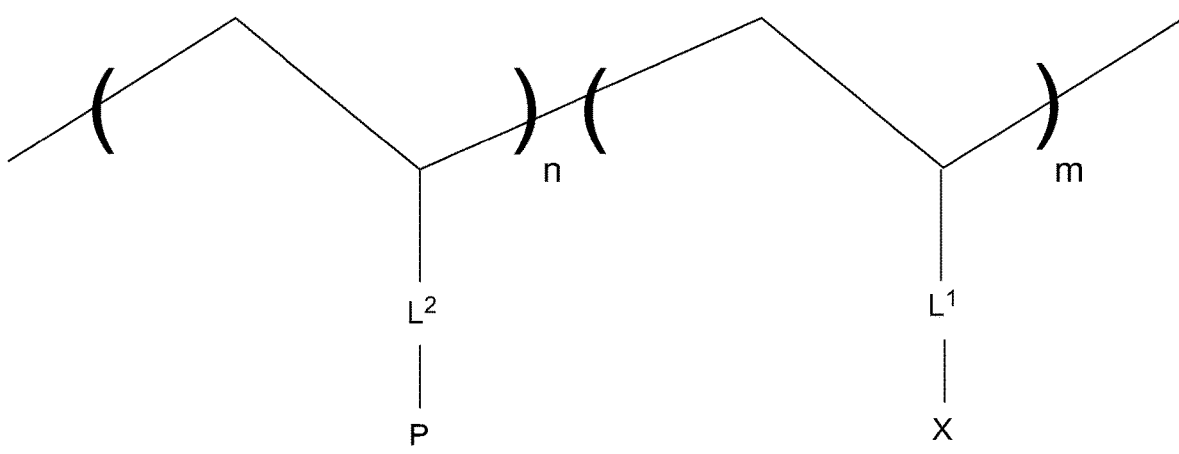
FIG. 2 illustrates schematically another representative embodiment of the generalized structure of an amphiphilic polymer hereof including a moiety X (COX inhibitor) and a hydrophilic polymer P.
Figure 3:
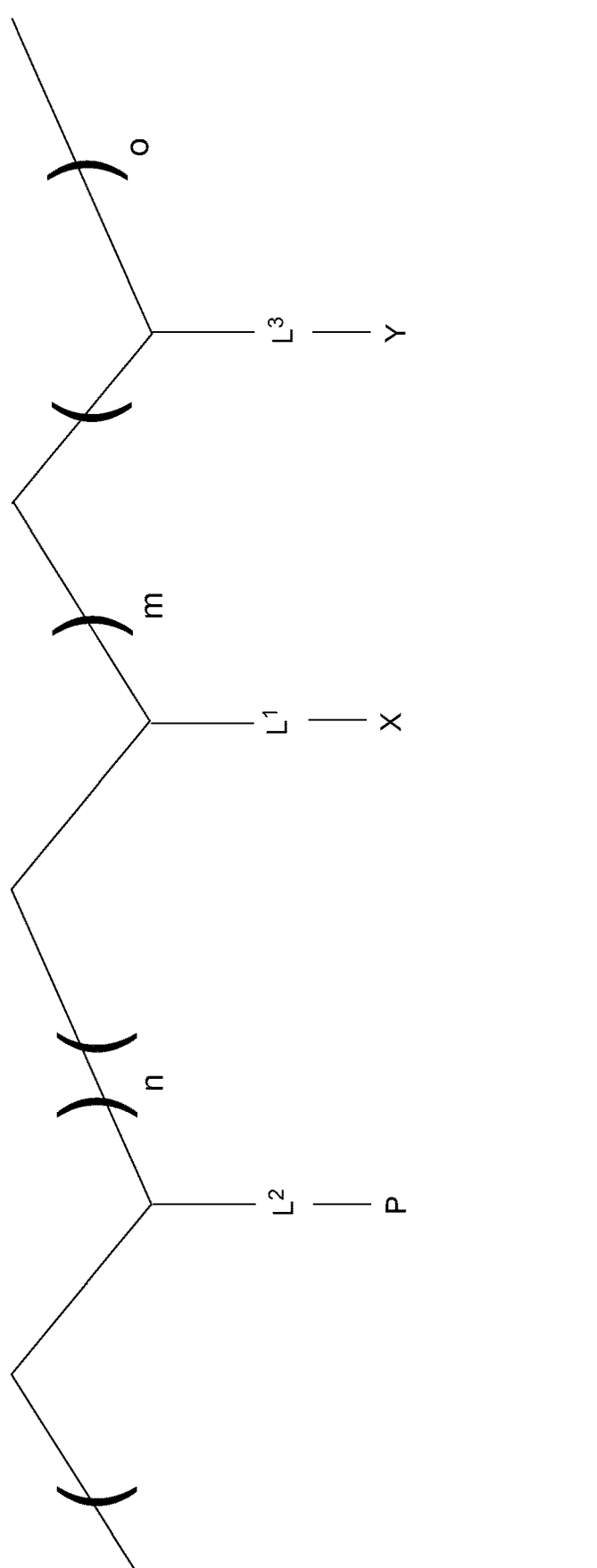
FIG. 3 illustrates schematically another representative embodiment of the generalized structure of an amphiphilic polymer hereof including a COX inhibitor moiety X, a hydrophilic polymer P and a targeting group or moiety Y.

FIGS. 1, 2 and 3 illustrate schematically embodiments of amphiphilic polymers hereof. The amphiphilic polymer may, for example, be formed via radical polymerization to have a hydrophobic polymer backbone. The hydrophobic polymer backbone may, for example, be formed via a free radical polymerization or via a reversible-deactivation radi- cal polymerization or RDRP (sometimes referred to as living polymerization, controlled radical polymerization or CRP).

Reversible-Deactivation Radical Polymerization (RDRP) procedures include, for example, Nitroxide Mediated Polymerization (NMP), Atom Transfer Radical Polymeriza- tion (ATRP), and Reversible Addition Fragmentation Trans- fer (RAFT) and others (including cobalt mediated transfer) that have evolved over the last two decades. RDRP provide access to polymer and copolymers comprising radically polymerizable/copolymerizable monomers with predefined molecular weights, compositions, architectures and narrow/ controlled molecular weight distributions. Because RDRP processes can provide compositionally homogeneous well- defined polymers, with predicted molecular weight, narrow/ designed molecular weight distribution, and high degrees of α- and ω-chain end-functionalization, they have been the subject of much study, as reported in several review articles and ACS symposia. See, for example, Qiu, J.; Charleux, B.; Matyjaszewski, K., *Prog. Polym. Sci.* 2001, 26, 2083; Davis, K. A.; Matyjaszewski, K. *Adv. Polym. Sci.* 2002, 159, 1; Matyjaszewski, K., Ed. Controlled Radical Polymerization; ACS: Washington, D. C., 1998; ACS Symposium Series 685. Matyjaszewski, K., Ed.; Controlled/Living Radical Polymerization. Progress in ATRP, NMP, and RAFT; ACS: Washington, D. C., 2000; ACS Symposium Series 768; and Matyjaszewski, K., Davis, T. P., Eds. Handbook of Radical Polymerization; Wiley: Hoboken, 2002, the disclosures of which are incorporated herein by reference.

The hydrophobic polymer backbone may be formed via radical polymerization of a variety of radically polymerizable monomers. Such monomers may, for example, include pendant groups as described herein prior to polymerization. Alternatively, such pendant groups may be attached after polymerization. Representative monomer for use herein include styrene, acrylic acid, methacrylic acid, vinyl mono- mers and their derivatives. In a number of embodiments, the degree of polymerization for hydrophobic polymers hereof is, for example, less than 200.

As described above, the polymer further includes a first plurality of pendant groups (X) attached to the hydrophobic polymer backbone and including a moiety attached via a labile bond which is cleavable in vivo to release a first therapeutic compound (for example, a COX inhibitor). Pen- dant group (X) may, for example, be a residue of a thera- peutic compound such as a COX inhibitor which is reacted with a functional group of a group on the polymer to attached (X) via a labile bond (thereby forming a prodrug). Therapeutic compound (X) includes one or more groups which interact ionically with a second therapeutic agent or compound which is discussed further below. Therapeutic compound (X) may further include one or more groups to interact via π-π bonding and/or hydrophobic interaction with the second therapeutic agent or compound. The polymer also includes a second plurality of pendant groups attached to the hydrophobic polymer backbone and including at least one hydrophilic polymer (P) which provides amphiphilicity to the polymer. In a number of embodiments, a plurality of the polymers self-assemble into micelles into which the second therapeutic agent/compound (for example, a chemothera- peutic agent/anticancer compound) may be loaded.

As illustrated in FIG. 3, the polymer may further include a third plurality of pendant groups (Y) attached to the hydrophobic polymer backbone. Groups (Y) may, for example, be selected to target a specific region of interest in vivo such as a tumor.

As illustrated in FIG. 1 through 3, pendant groups (X), (P) and (Y) may, for example, independently be attached to the hydrophobic polymer backbone via a linking moiety (L$^1$), (L$^2$) and (L$^3$). In a number of embodiments, such a linking moiety may provide additional functionality. In a number of embodiments, such a linking moiety may include a bond that is labile in vivo if it is desirable to releasable connected the pendant group. As set forth above, it is desirable that pendant group (X) be cleavable or releasable in vivo to optimize the activity of the first therapeutic compound in vivo. It may, for example, be desirable to cleave targeting group (Y) if such a group also has in vivo therapeutic or diagnostic activity. It may, for example, be desirable to cleave hydrophilic poly- mer group (Y) if it is desirable to cause self-assembled structures such as micelles formed by the polymers hereof to disassemble at a certain point and/or to facilitate clearance of the carriers hereof from the body. The conditions and timing of cleaving of labile bonds hereof may be controlled via the selection of such bonds as known to those skilled in the chemical arts.

In a number of embodiments, a linking moiety as described above may include at least one group which is interactive via hydrophobic interaction, π-π stacking or ionic interaction. Groups interactive via π-π stacking may, for example, include an aromatic group. In a number of embodiments, groups interactive via π-π stacking include a benzyl group. Linking moieties including various function- alities are, for example, described in PCT International Patent Application Publication No. WO 2020/077170, the disclosure of which is incorporated herein by reference.

The first plurality of pendant groups (X) may, for example, be attached to the hydrophobic polymeric backbone via a first linking group ($L^1$). The first linking group ($L^1$) may, for example, include at least a first group which is interactive with the therapeutic compound. In a number of embodiments, the first linking group ($L^1$) includes a labile group or bond which is labile or cleavable in vivo as described above. The second plurality of pendant groups may also be independently attached to the hydrophobic polymer backbone via a second linking group ($L^2$). The second linking group ($L^2$) may be absent and the hydrophilic polymer may be directly attached to the hydrophobic polymer backbone. The second linking group ($L^2$) may, for example, independently include at least a one group interactive with the therapeutic compound. The third plurality of pendant groups may likewise be independently attached to the hydrophobic polymer backbone via a third linking group ($L^3$). The third linking group ($L^3$) may be absent and the hydrophilic polymer may be directly attached to the hydrophobic polymer backbone. The third linking group ($L^3$) may, for example, independently include at least a one group interactive with the therapeutic compound.

In the case that a group hereof is capable to interact via $\pi$-$\pi$ stacking/interaction, the group may, for example, be an aromatic group. In general, aromatic groups are cyclic molecules including resonance bonds that exhibit increased stability compared to other geometric or connective arrangements with the same set of atoms. Aromatic groups include, for example, benzyl and naphthyl groups. In a number of embodiments hereof, aromatic groups hereof are benzyl groups.

The hydrophilic oligomer(s) or hydrophilic polymer(s) in the compositions hereof may, for example, be selected from the group consisting of hyaluronic acid, glucan, chitosan, a polyalkylene oxide, a polyvinylalcohol, a polyacrylic acid, a polyacrylamide, a polyoxazoline, a polysaccharide and a polypeptide. In a number of embodiments, the at least one hydrophilic polymer is a polyalkylene oxide. The polyalkylene oxide may, for example, be a polyethylene glycol. A polyethylene glycol or other hydrophilic polymer hereof may, for example, have a molecular weight of at least 500 Da. In a number of embodiments, the polyethylene glycol of other hydrophilic polymer hereof has a molecular weight in the range of 100 Da to 5 KDa or in the range of 500 Da to 2 KDa.

As described above, pendant groups hereof such as the first plurality of pendant groups, the second plurality of pendant groups and/or the third plurality of pendant groups may, for example, be attached to the hydrophobic polymer backbone via a direct coupling or via a linking group (for example, to provide additional functionality). Once again, pendant groups hereof may be attached via a group or bond that is labile. The group or bond that is labile (in vivo) may, for example, include at least one of a hydrolytically labile group, a reductive sensitive linkage, a pH-sensitive linkage, a ROS-sensitive linkage, a hypoxia-sensitive linkage, or an enzyme/protease-sensitive linkage. The labile linking group may, for example, be labile under acidic pH conditions. The pH sensitive or acid-labile bond may, for example, include a carboxydimethyl maleate, a hydrazine, an imine, an acetal, an oxime, a silyl ether, a cis-asonityl, a ketal or another pH or acid-labile bond or linkage. Use of a labile bond that is sensitive to acidic conditions may be used to cleave the pendant group in, for example, an acidic tumor environment. In a number of embodiments, the labile linking group is sensitive to reductive such as a disulfide bond. In a number of embodiments, the hydrolytically labile group includes an ester group, an orthoester group, a thioether-ester group, an anhydride group, an amide group (for example, peptide groups), or a carbonate group. ROS-sensitive labile bonds or linkages include, for example, a thioketal bond. An enzyme or protease-sensitive bond or linkage includes, for example, a protease cleavable peptide including the sequence CGLDD which is labile in response to the presence of matrix metalloproteinases MMP-2 or MMP-9. The labile bond may be selected in a manner to control the rate of release of the pendant group attached to the hydrophobic backbone via the labile bond.

Figures 4A, 4B:
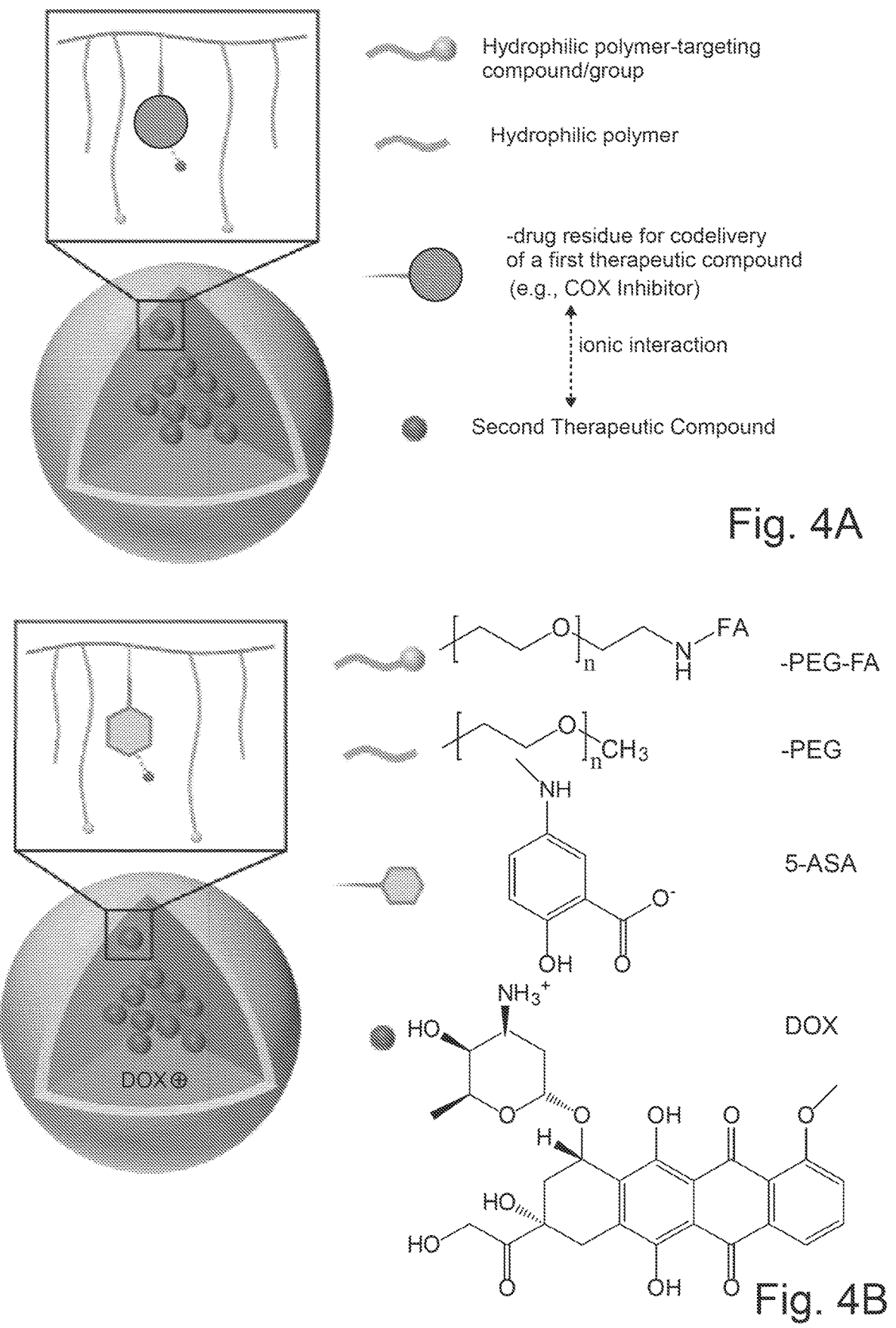
FIG. 4A illustrates an idealized schematic representation of a compound or drugs loaded onto a micelle carrier structure formed with a plurality of the polymers hereof wherein DOX and 5-ASA are located in the core of the nanoparticles with PEG and PEG-FA shielding outside.
FIG. 4B illustrates an idealized schematic representation of doxorubicin (DOX) loaded onto a micelle carrier structure formed with a plurality of the polymers hereof including the COX inhibitor 5-aminosalycilic acid or 5-ASA and folic acid (FA).
Figure 4C:
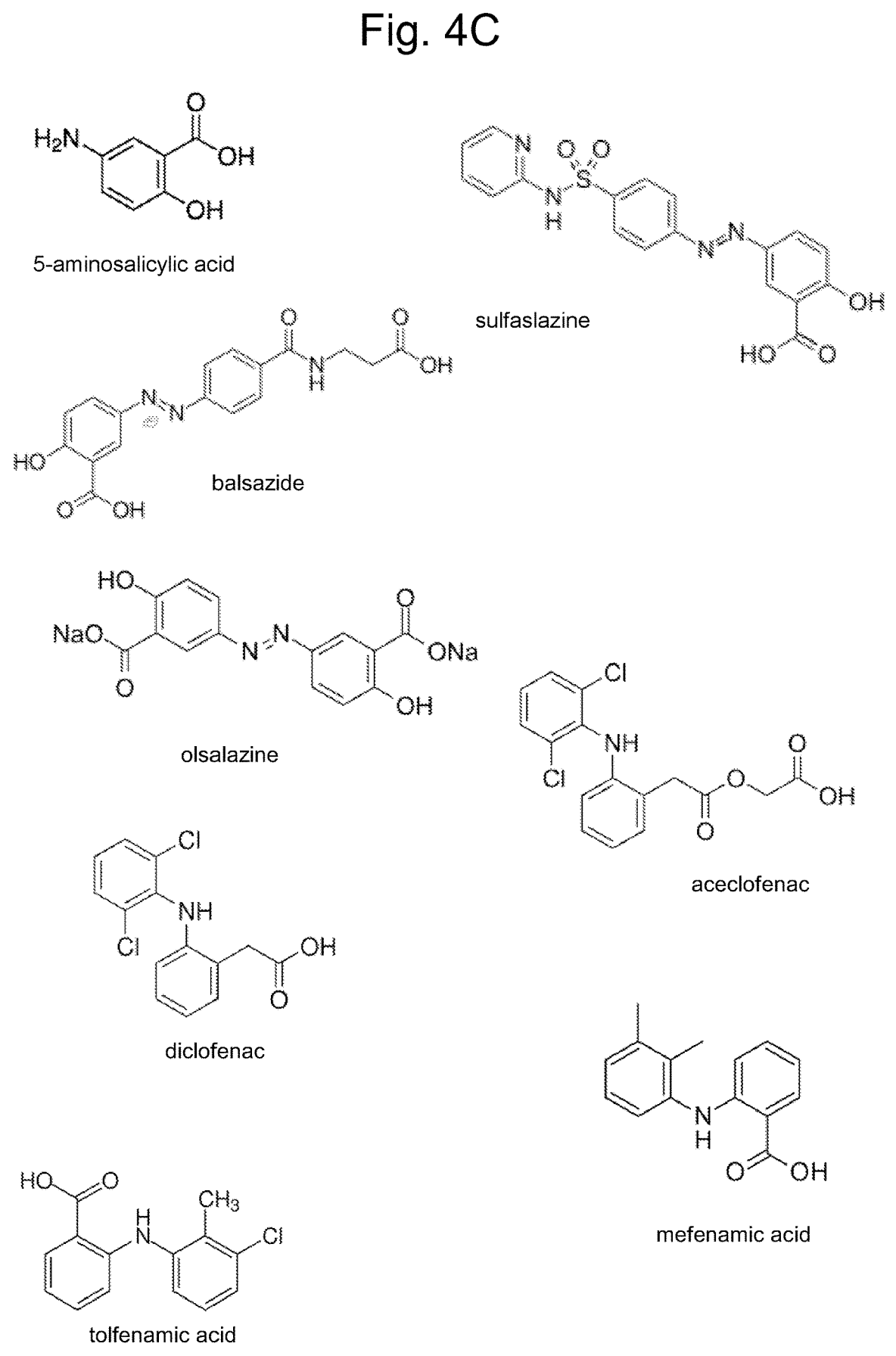
Figure 4D:
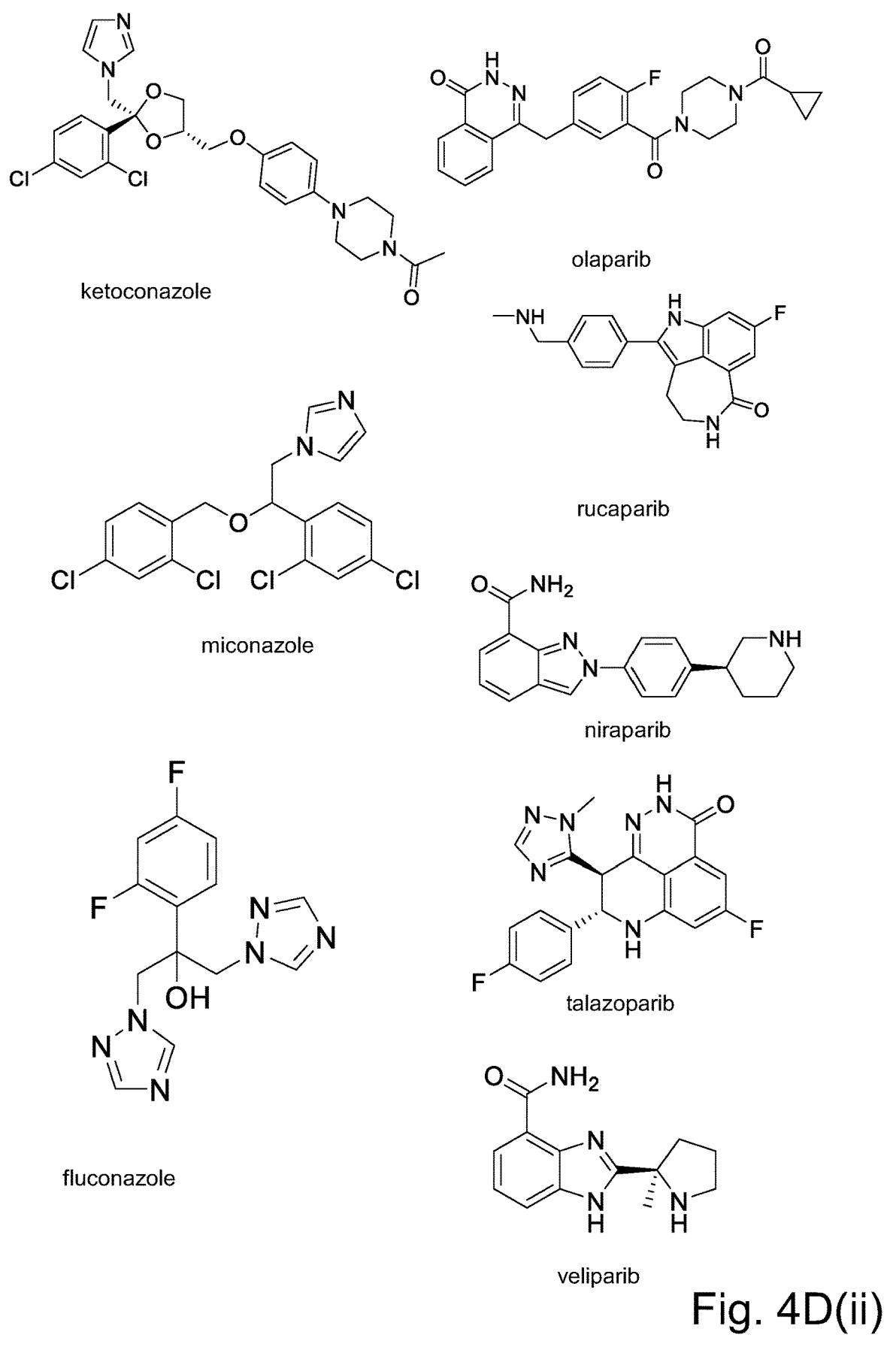

FIG. 4A sets forth an idealized schematic representation of at least a second therapeutic agent, compound or drug (which may, for example, be an anticancer or chemotherapeutic compound) loaded onto a micelle carrier structure formed with a plurality of the polymers hereof. As used herein, a therapeutic agent, compound or drug is a biologically active substance which has an effect on the body (for example, a medicinal or therapeutic effect, an intoxicating effect, a performance enhancing effect or another effect). A therapeutic compound or agent may, for example, be an antibody, an antibiotic, an antiviral, an antimycotic, an anticancer agent, an immunomodulating agent, a chemotherapeutic agent, an anti-rejection agent, an analgesic agent, an antifungal, or an anti-inflammatory agent. In a number of embodiments, the first therapeutic compound is a COX inhibitor. FIG. 4B illustrates an idealized schematic representation similar to FIG. 4A wherein doxorubicin (DOX) is loaded into a micelle carrier structure formed with a plurality of the polymers hereof which include a labile moiety releasable to provide the representative COX inhibitor 5-aminosalycilic acid or 5-ASA or a biologically active analogue thereof. In the embodiment of FIG. 4B, folic acid (FA) is included as a targeting group. A number of representative COX inhibitors for use in the present invention are illustrated in FIG. 4C. Representative compounds for the second therapeutic compounds hereof are illustrated in FIGS. 4D(i) and 4D(ii).

Without limitation to any mechanism, and with reference to, for example, FIGS. 4A and 4B, it is hypothesized that an inwardly oriented hydrophobic domain is created during micelle formation via the hydrophobic backbone of the polymers hereof, which may orient via intrachain hydrophobic interactions to assume a folded conformation. Pendant aromatic groups, when present in, for example, linking groups hereof, may increase hydrophobicity and assist in forming the hydrophobic domain and in $\pi$-$\pi$ interactions with one or more hydrophobic therapeutic or other compounds loaded within the hydrophobic domain. It was further hypothesized that an outwardly oriented hydrophilic domain was formed by the hydrophilic polymer side chains.

Nanoparticles/micelles formulated from polymers hereof may, for example, be prepared by a facile film hydration method, and may have small diameters/size (for example, less than 150 nm, less than 100 nm, no greater than 80 nm, or no greater than 70 nm, high drug loading capacity (for example, 42.3% for DOX) and excellent stability. In a number of embodiments, the drug loading capacity is in the range of 1-50% by weight, at least 4-50% by weight, at least 10-50% by weight or at least 20-50% by weight. In vivo data shows that formulations hereof significantly improved therapeutic effect compared to free drugs or corresponding free drug combinations.

Particle size of an injectable carrier is a very important physicochemical parameter to be considered because it plays a vital role in the cellular uptake, biodistribution and tumor penetration. As also described above, it has been reported that nanoparticles with diameter range of 4~200 nm have long circulation time and can efficiently accumulate in the tumors as a result of an enhanced permeability and retention (EPR) effect. Nanoparticles less than 4 nm are rapidly excreted by the kidney, while nanoparticles larger than 200 nm tend to be taken up by the reticuloendothelial system (RES). Moreover, accumulating evidence indicates that nanomedicines with small sizes exhibit superior tumor penetration and enhanced anti-tumor activity.

In a number of representative studies hereof, the cytotoxicity of the representative COX inhibitor 5-aminosalicylic acid (5-ASA), alone or in combination with the representative chemotherapeutic agent doxorubicin (DOX) in several human and murine cancer cell lines was studied. Further, the antitumor activity of 5-ASA in vivo using two murine tumor models (4T1.2 and CT26) was studied at different expression levels of COX. To facilitate the in vivo evaluation of the combination therapy, a 5-ASA prodrug polymer-based nanocarrier hereof was developed to facilitate selective codelivery of 5-ASA and DOX. In addition to examination of antitumor activity, the underlying mechanism was investigated.

Figure 5:
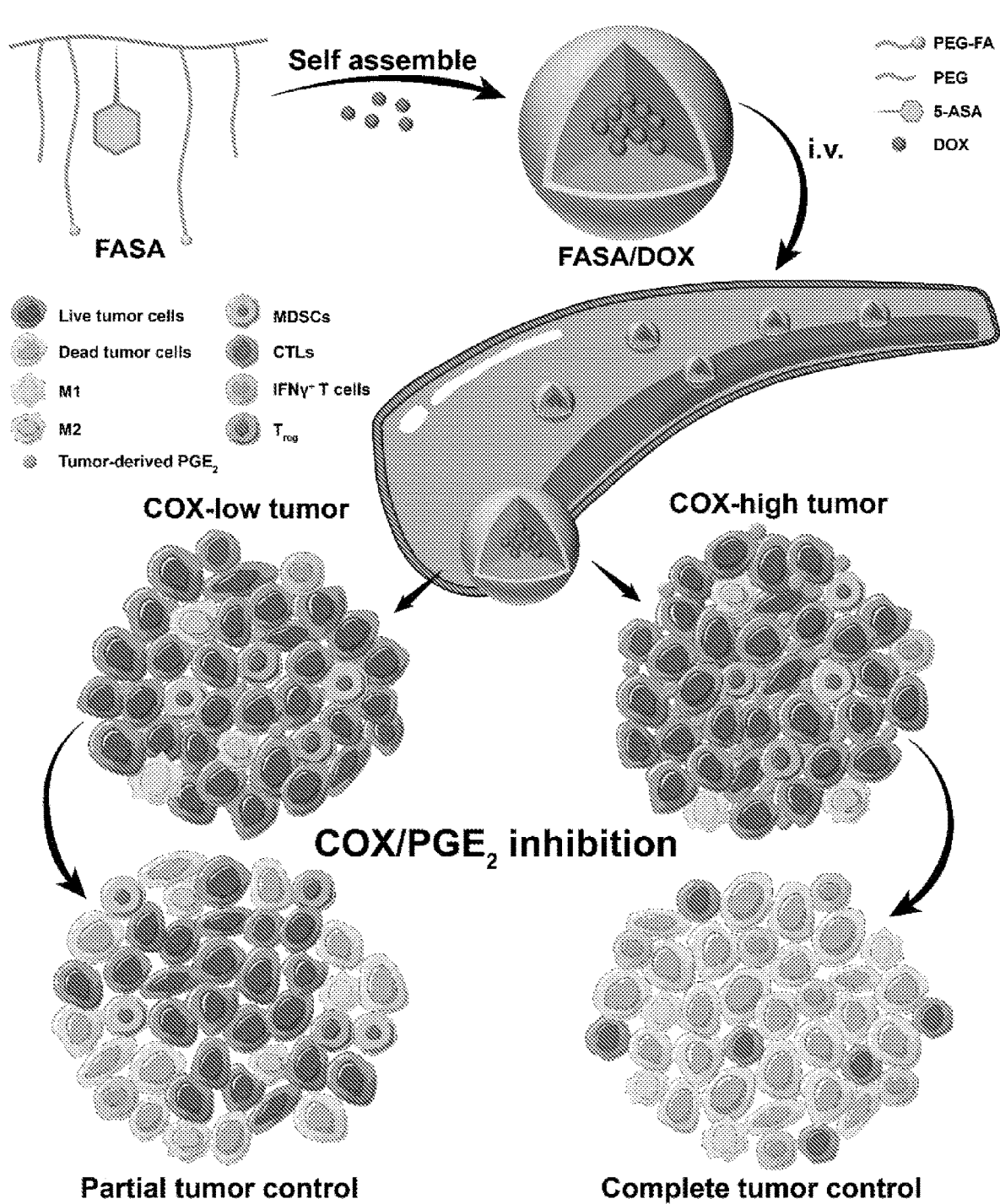
FIG. 5 illustrates schematically an idealized mechanism of delivery and function of the carrier/drug combination of FIG. 4B.

5-ASA (a COX inhibitor) prodrug-based amphiphilic polymers (PASA and FASA) hereof well retain the pharmacological activity of 5-ASA. Further, such polymers self-assemble to form a small-sized nanocarrier (~70 nm) that is highly effective in loading, for example, doxorubicin (DOX) and/or other anticancer agents and achieving selective codelivery of both 5-ASA and DOX and/or other anticancer agents to tumors. FIG. 5 illustrates an idealized illustration of the differential effects of FASA/DOX in modulating the immune microenvironment of COX-low and COX-high tumors. Self-assembled FASA/DOX nanoparticles are administered i.v. and selectively accumulated to the tumor by EPR effect and folate-mediated active targeting. FASA/DOX was more effective in improving the immune microenvironment of COX-high tumors, leading to better control of tumor growth.

Figure 6A:
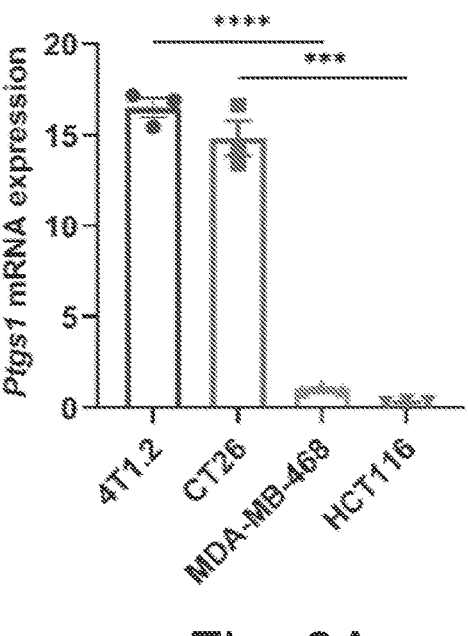
FIG. 6A illustrates Ptgs1 mRNA expression levels of 5-ASA and DOX in tumor cell lines (4T1.2, CT26, MDA-MB-468 and HCT116).
Figure 6B:
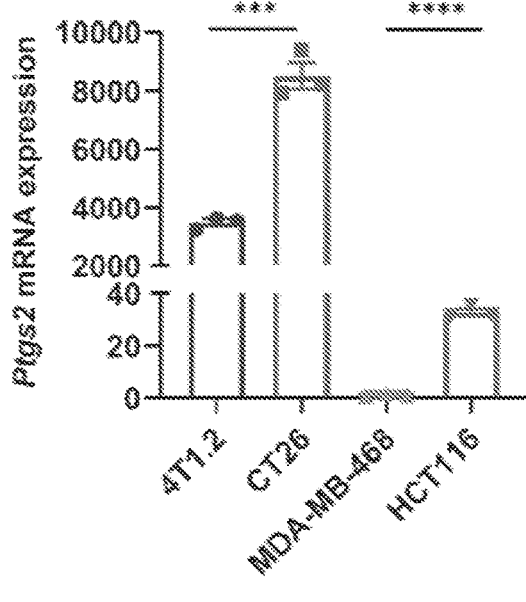
FIG. 6B illustrates Ptgs2 mRNA expression levels of 5-ASA and DOX in tumor cell lines (4T1.2, CT26, MDA-MB-468 and HCT116).
Figure 6C:
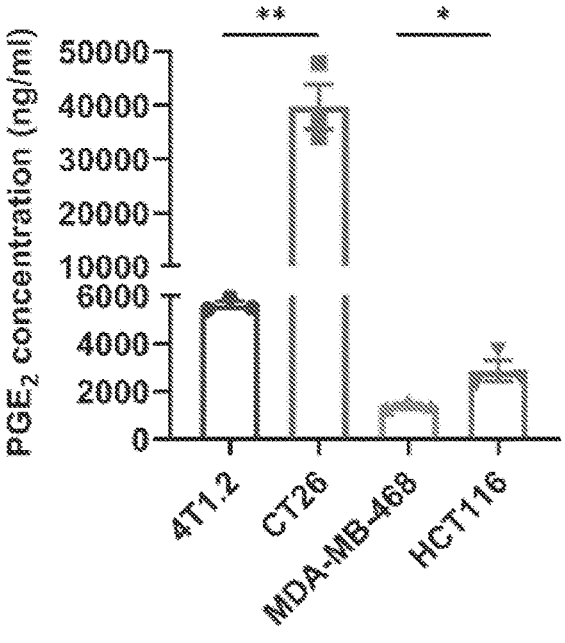
FIG. 6C illustrates $PGE_2$ concentration in the cell culture supernatant in tumor cell lines (4T1.2, CT26, MDA-MB-468 and HCT116).
Figure 6D:
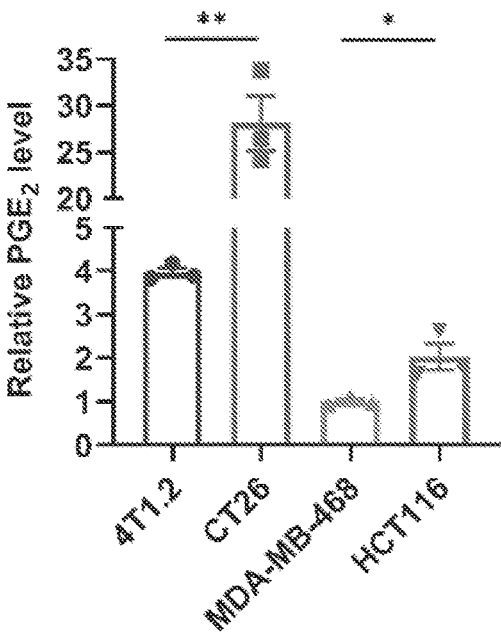
FIG. 6D illustrated relative $PGE_2$ level in tumor cell lines (4T1.2, CT26, MDA-MB-468 and HCT116)

To elucidate a potential role of tumor cells-derived COX-1/2 (encoded by Ptgs1/2) in 5-ASA-mediated antitumor activity, the mRNA expression levels of Ptgs1 and Ptgs2 were studied in 4 cancer cell lines including murine breast cancer cell line 4T1.2, murine colon cancer cell line CT26, human breast cancer cell line MDA-MB-468 and human colon cancer cell line HCT116. As shown in FIGS. 6A and 6B, all 4 cancer cell lines examined had higher levels of Ptgs2 mRNA compared to their Ptgs1 mRNA counterparts. For either colon or breast cancer type, the murine cell line examined expressed higher levels of both Ptgs1 and Ptgs2 compared to the human cell line of the same cancer type. Finally, the murine colon cancer cell line CT26 showed higher mRNA level of COX-2 than the murine breast cancer cell line 4T1.2. FIGS. 6C and 6D show that supernatants from CT26 cells had the highest level of $PGE_2$. The amounts of $PGE_2$ in the culture medium follows the order of CT26>4T1.2>HCT116>MDA-MB-468. These data suggest the COX enzymatic activities in the 4 cell lines examined were consistent with their Ptgs1/2 mRNA levels, particularly the expression levels of Ptgs2.

Figures 6E, 6F, 6G, 6H:
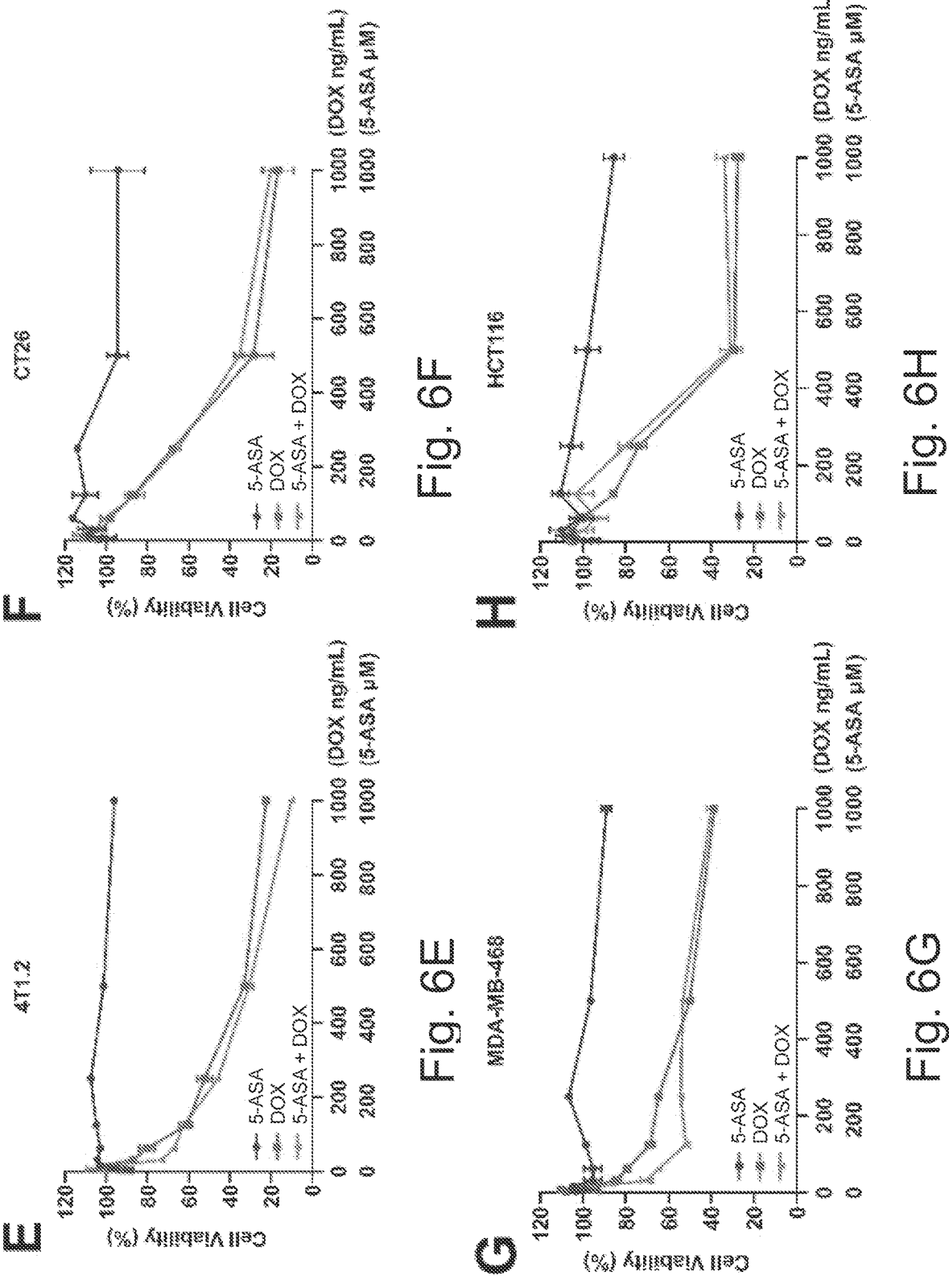
FIG. 6E illustrates proliferation inhibition of 4T1.2
FIG. 6F illustrates proliferation inhibition of CT26.
FIG. 6G illustrates proliferation inhibition of MDA-MB-468.
FIG. 6H illustrates proliferation inhibition of HCT116, tumor cell lines were treated with various concentrations of free 5-ASA, free DOX or the combination of 5-ASA and DOX in the studies of FIGS. 6A through 6H, and, after 48 h, the cytotoxicity was determined by MTT assay; and wherein all data represent the means±SEM (n=3), and p values were determined by two-tailed Student's t-test. *p<0.05, p<0.01, *p<0.001, ****p<0.0001.

FIGS. 6E and 6H show the in vitro cytotoxicity of 5-ASA, alone or in combination with DOX in the 4 cancer cell lines. A concentration range of 0~1 mM was chosen as the production of $PGE_2$ can be inhibited by 80% when 5-ASA concentration reached 1 mM. 5-ASA did not show any significant anti-proliferation effect on all four cell lines examined (FIGS. 6E-6H) at the concentrations used. In addition, no improvement in cytotoxicity was noticed upon combination of 5-ASA with DOX. Several studies have demonstrated that the anti-inflammatory activity from COX inhibition can suppress tumor growth in vivo, either alone or in combination with other modalities. Therefore, the in vivo antitumor activity of 5-ASA, alone or in combination with DOX, was further examined in the two murine cancer models (4T1.2 and CT26) that have different levels of COX activities. To better elucidate a role of tumor-derived $PGE_2$ in the antitumor effect, a 5-ASA prodrug-based nanocarrier (PASA) was designed to achieve enhanced selective delivery of 5-ASA or codelivery of 5-ASA and DOX to tumor tissues. In addition, folate was introduced into the carrier to further improve the selective delivery to tumors.

Figures 7A, 7B:
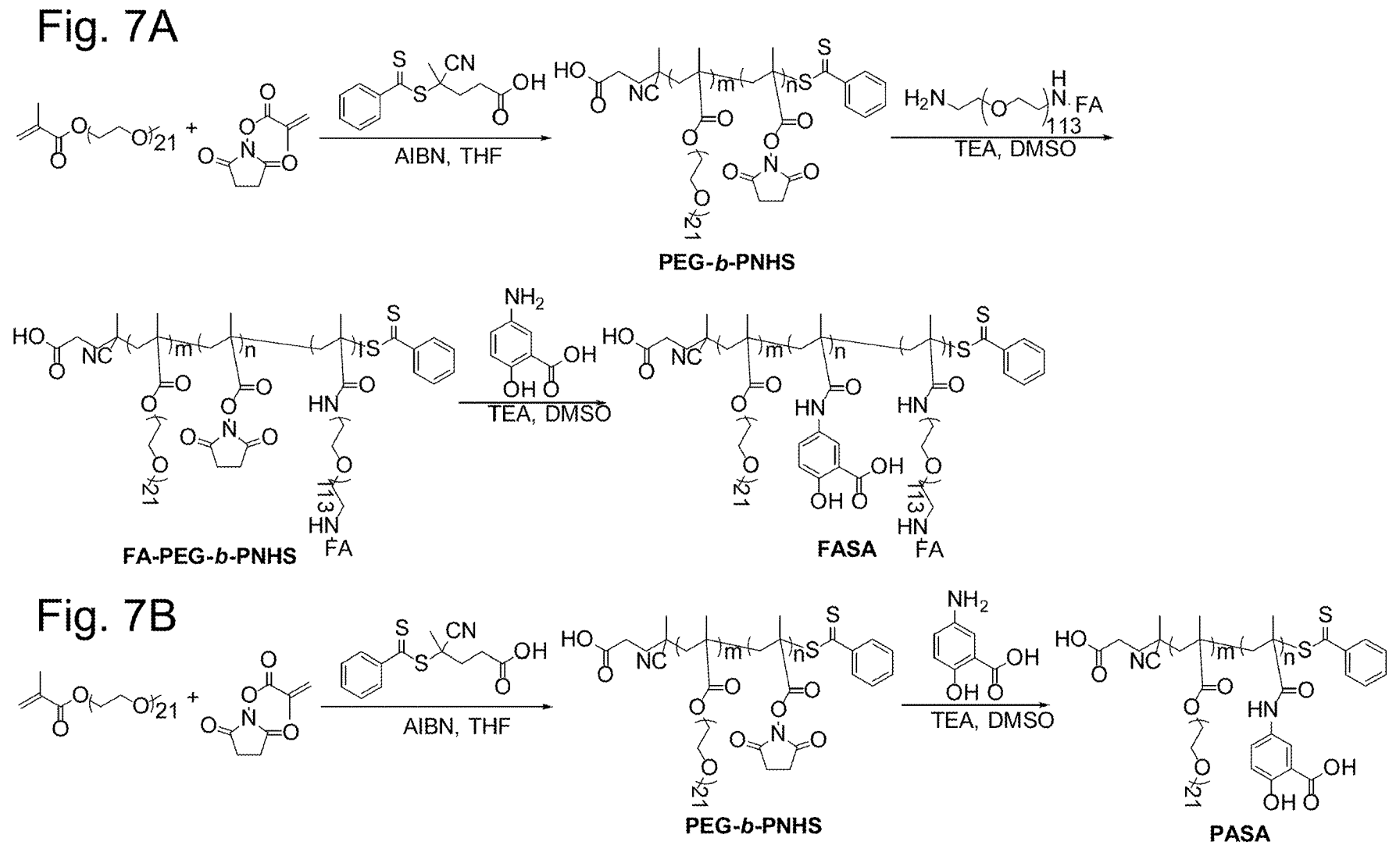

In a number of representative studies hereof, prodrug-based amphiphilic polymers (PASA, illustrated in FIG. 7B, and FASA, illustrated in FIG. 7A) were synthesized with COX inhibitor pharmacological properties for a proposed treatment of colorectal cancer as well as other cancers through targeting inflammatory prostaglandin production. First, PEG-b-PNHS polymer was synthesized through reversible addition—fragmentation chain-transfer (RAFT) polymerization with $PEG_{950}$ and N-Succinimidyl Methacrylate. 5-ASA was subsequently conjugated to PEG-b-PNHS to yield PASA. FASA polymer was also obtained through reaction of PEG-b-PNHS with folate-PEG-$NH_2$ followed by reaction with 5-ASA. A relatively long PEG spacer (3.5 K) was introduced between folate and PASA polymer to overcome any potential steric hindrance for interaction with folate receptor (FR) on FR-overexpressing tumor cells. All the peaks of the polymers, PEG-b-PNHS, PASA, FA-PEG-b-PNHS and FASA, were well assigned in $^1$H-NMR. For PEG-b-PNHS polymer, the average degree of polymerization of the $PEG_{950}$ monomer was calculated to be 8 according to the conversion of $PEG_{950}$ monomer. The average units of the NHS (N-Hydroxysuccinimide) monomer were determined to be 64. After conjugation of 5-ASA to PEG-b-PNHS polymer, the characteristic peaks of benzene ring were observed in the $^1$H-NMR at 6.56, 7.39 and 7.85 ppm. By comparing these three peak intensities at 6.0-8.0 ppm with proton intensities of methoxy in PEG at 3.24 ppm, the average ratio of 5-ASA to $PEG_{950}$ was about 4:1, both in PASA and FASA. The molar substitution of folate in FASA was 2%, which was identified by methylene of PEG (3.51 ppm) linked to folate.

Figures 8A, 8B, 8C, 8D:
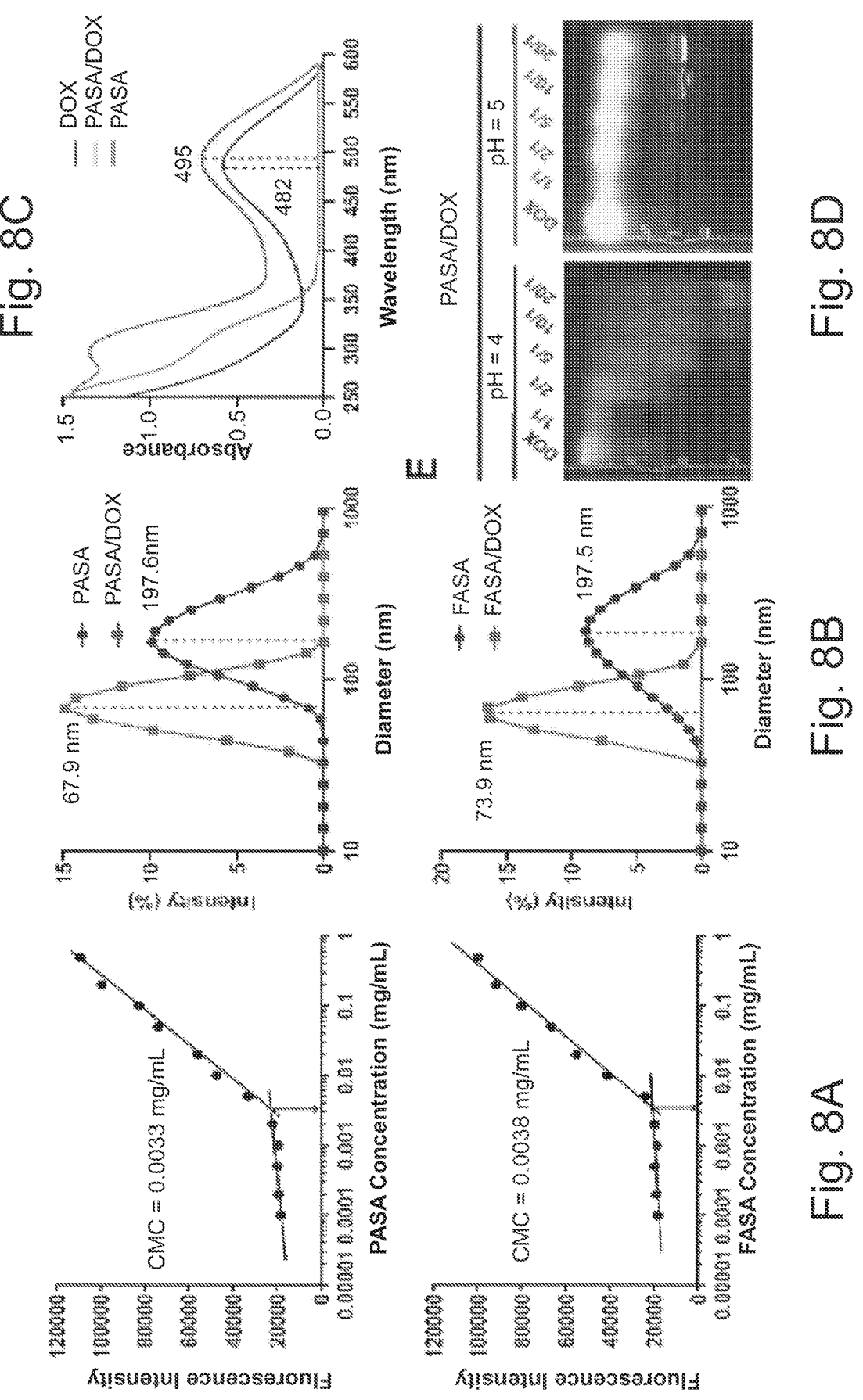
FIG. 8A illustrates critical micelle concentration determinations of PASA and FASA polymers.
FIG. 8B illustrates size distribution studies of blank PASA, FASA and PASA/DOX, FASA/DOX micelles at a carrier/drug ratio 10/1 (mg/mg).
FIG. 8C illustrates UV/Vis absorbance spectra of DOX, PASA/DOX and PASA in aqueous solution, wherein the carrier/drug ratio was at 10/1 (mg/mg).
FIG. 8D illustrates gel electrophoresis of PASA/DOX at various ratios.

Both PASA and FASA are amphiphilic molecules and can potentially self-assemble to form micellar carriers that can load other hydrophobic drugs, suggesting a 5-ASA polymer-based new carrier platform for codelivery of 5-ASA and other drugs such as DOX (see FIGS. 4A and 4B). FIG. 8A shows that PASA and FASA had a CMC of 0.0033 mg/mL and 0.0038 mg/mL, respectively. The relatively low CMCs suggest a likely excellent stability of PASA and FASA micelles after dilution in blood following i.v. administration. FIG. 8B shows that PASA and FASA polymers formed blank micellar particles of around 197.6 nm and 197.5 nm, respectively. Interestingly, incorporation of DOX into micelles resulted in significant decreases in nanoparticle sizes and the sizes of the particles deceased gradually with an increase in the DOX/polymer ratio (see FIG. 8E). At a polymer/DOX ratio of 1/1 (w/w), the sizes of DOX-loaded PASA and FASA were 67.9 and 73.9 nm, respectively. Without limitation to any mechanism, it was hypothesized that this result is likely due to several interactions between polymer and DOX, including strong ionic interaction, π-π stacking and hydrophobic interaction, leading to the formation of a more compact structure. Indeed, the UV-Vis spectrum (FIG. 8C) showed a characteristic absorbance of free DOX at approximately 482 nm, whereas a 13 nm red-shift was observed in the PASA/DOX, likely due to Van der Waal's interaction between the polymer and DOX. The DOX electrophoresis (FIG. 8D) results showed that, under physiological pH 7.4, DOX stayed associated with PASA carrier when PASA/ DOX ratio reached 5:1 or higher. In contrast, an obvious release of DOX was observed at pH 5 even at a PASA/DOX ratio as high as 20/1, which might be ascribed to a significant reduction in the ionization of 5-ASA at an acidic condition. FIG. 8E illustrates Table 1 setting forth biophysical properties of DOX-loaded micelles at various carrier/drug ratios. At a PASA/DOX weight ratio of 1/1, an unprecedently high drug loading capacity (DLC) of over 40% was achieved with a drug loading efficiency (DLE) of 82.18%. The DOX-loaded micelles were stable at room temperature (RT) for over seven days (FIG. 8E). Similar results were obtained for FASA/DOX (FIG. 8E). Similar results were also obtained when PASA was used to formulate imatinib that has several amines in the structure (data not shown). However, PASA was not as effective in formulating several other hydrophobic agents tested such as paclitaxel and curcumin highlighting the advantage of ionic interaction for PASA-based nanocarriers hereof.

The release kinetics of DOX from DOX-loaded PASA and FASA micelles were evaluated by dialysis method using two different mediums under physiological (pH 7.4) or acidic (pH 5) condition at 37° C. As depicted in FIG. 8F, free DOX was rapidly diffused across the dialysis membrane. Under physiological pH (7.4), less than 10% of DOX was released from PASA or FASA micelles in 2 h and a slow kinetics of release was extended over 72 h. Instead, DOX was released much more rapidly under pH 5: around 20% of DOX was released in 2 h, and over 40% was released in 12 h. These data are consistent with the results of electrophoresis, likely due to a disruption of the interaction of the carrier with DOX under acidic condition. This pH-sensitive DOX release profile of our system suits well its application for drug delivery to tumors via i.v. route due to its excellent stability in blood but accelerated drug release upon reaching the acidic tumor environment, particularly the endosomal/lysosomal compartment after intracellular delivery.

Figures 9A, 9B, 9C:
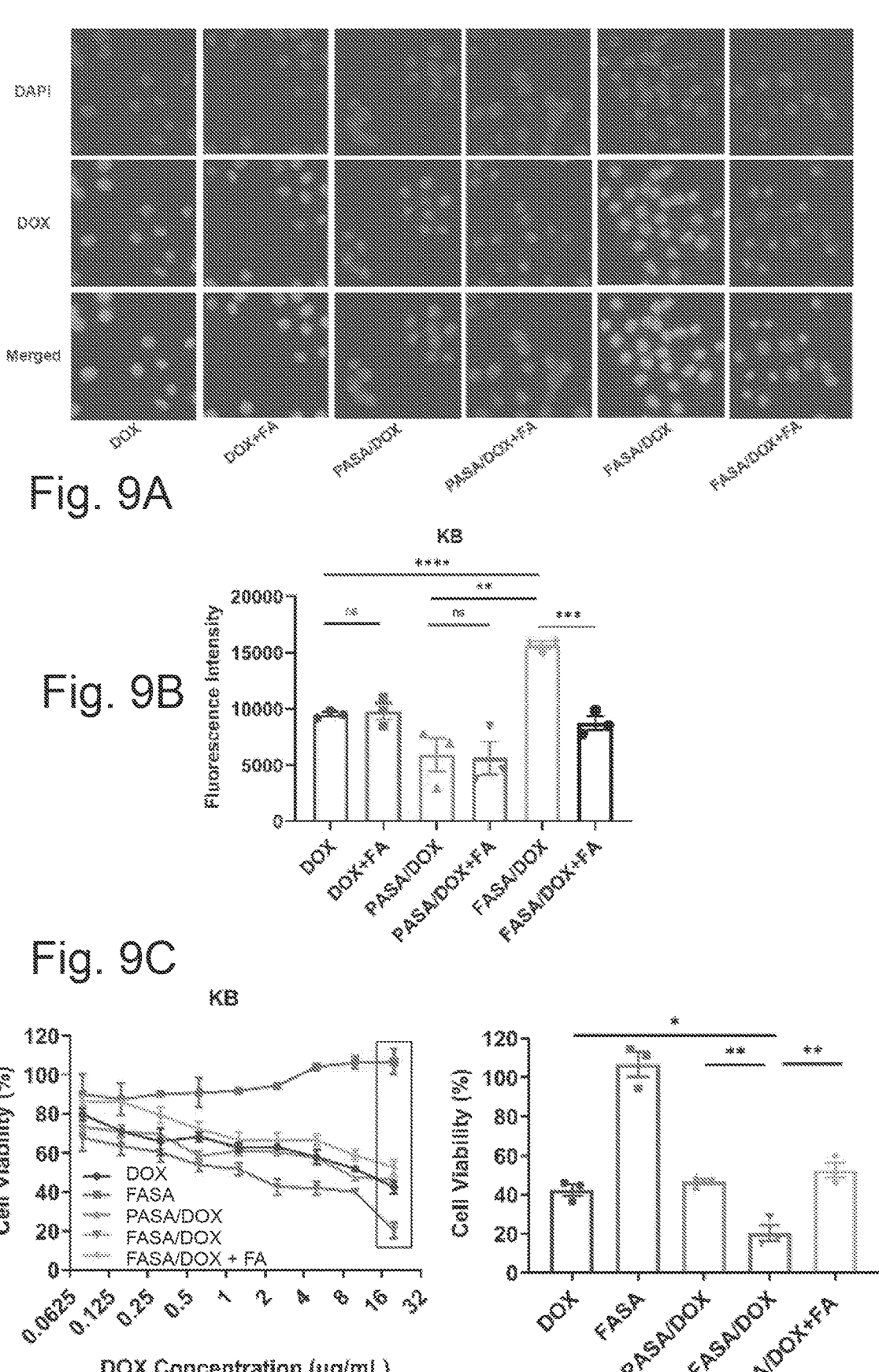
FIG. 9A illustrates fluorescence microscope images of KB cells after incubation with different DOX formulations for 30 min.
FIG. 9B illustrates corresponding fluorescence quantification results from FIG. 9A by flow cytometry wherein DOX concentration was 6 μg/mL.
FIG. 9C illustrates cytotoxicity of DOX-loaded 5-ASA based micelles and cell viability at highest concentration (histogram) in KB cell line after 48 h treatment.
Figures 9D, 9E, 9F, 9G:
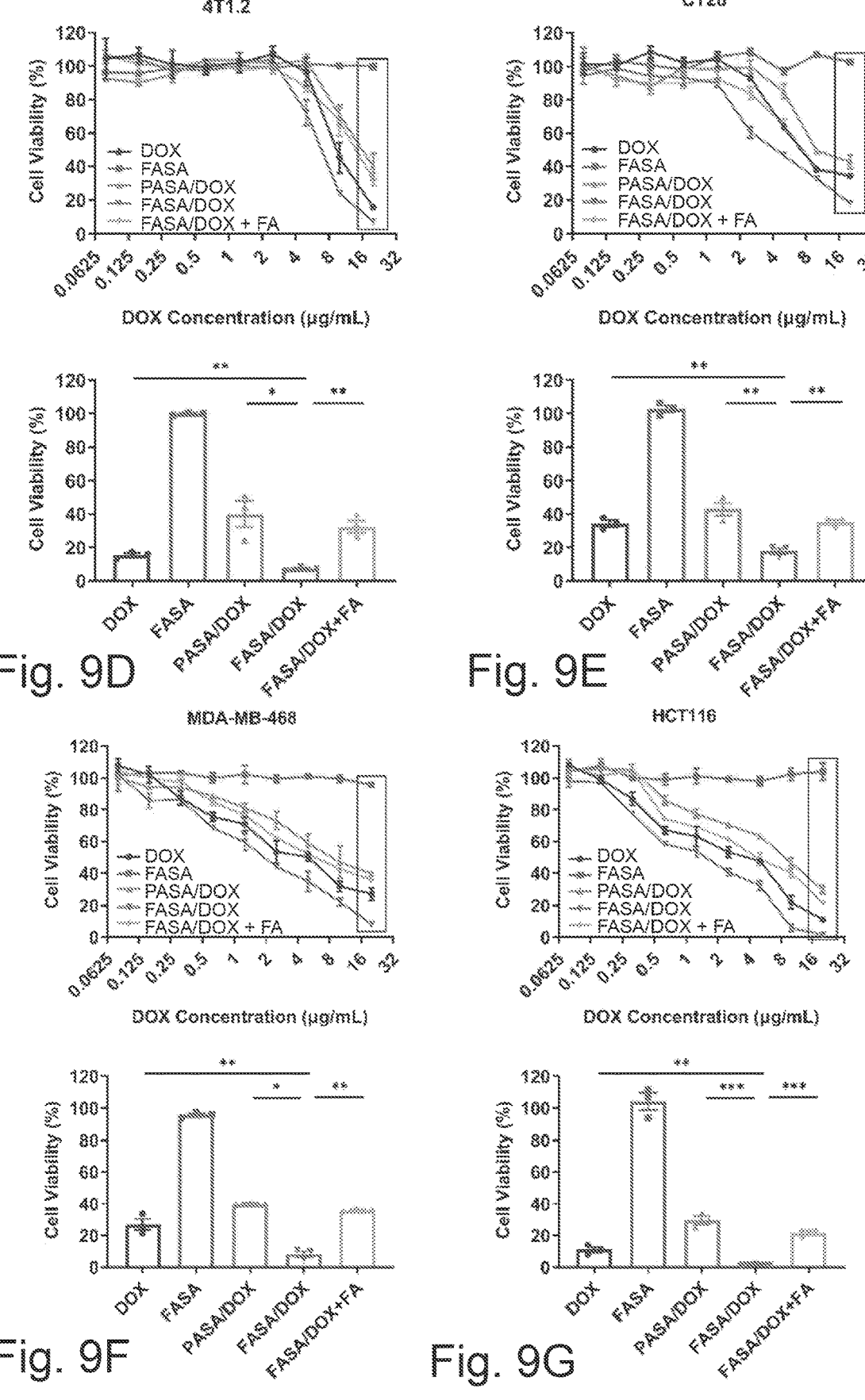
FIG. 9D illustrates cytotoxicity of DOX-loaded 5-ASA based micelles and cell viability at highest concentration (histogram) in 4T1.2 cell line after 48 h treatment.
FIG. 9E illustrates cytotoxicity of DOX-loaded 5-ASA based micelles and cell viability at highest concentration (histogram) in CT26 cell line after 48 h treatment.
FIG. 9F illustrates cytotoxicity of DOX-loaded 5-ASA based micelles and cell viability at highest concentration (histogram) in MDA-MB-468 cell line after 48 h treatment.
FIG. 9G illustrates cytotoxicity of DOX-loaded 5-ASA based micelles and cell viability at highest concentration (histogram) in HCT116 cell lines after 48 h treatment, wherein the experiments of FIGS. 9A through 9F were performed in triplicate and repeated three times, data are presented as means±SEM, p values were determined by two-tailed Student's t-test, and *p<0.05, p<0.01, *p<0.001, ****p<0.0001, ns, no significance.

KB cells were chosen to investigate the cellular internalization of various DOX formulations, particularly the folate-mediated active targeting as these cells are known to overexpress folate receptor α (FRα). KB cells were treated with different DOX formulations with or without free folate at 37° C. and then observed by fluorescence microscope. After 30 min treatment free DOX was efficiently taken up by KB cells and the fluorescence signal was largely found in the nucleus (FIG. 9A). Incorporation of DOX into PASA micelles led to a decrease in the cellular uptake. However, the cellular uptake was significantly improved following conjugation with folate. The level of cellular uptake of FASA/DOX was even higher than that of free DOX. The improvement in cellular uptake was substantially abolished in the presence of excess amount of free folate (100 μM). Free folate had no effect on the uptake of free DOX or PASA/DOX, suggesting that the enhanced cellular uptake of FASA/DOX was largely mediated by the FR.

The cellular uptake of various DOX formulations was further investigated by flow cytometry (FIG. 9B). The data of the quantitative flow cytometric assay were consistent with the results of fluorescence microscopic examination. Similar results were observed in other four tumor cell lines (4T1.2, CT26, MDA-MB-468, and HCT116). However, a much lower magnitude of improvement in cellular uptake was seen for the folate-decorated FASA/DOX in all the 4 cell lines examined likely due to a much lower expression levels of the FR in these cell lines compared to KB cells.

The in vitro cytotoxicity of various DOX formulations was evaluated in several cell lines by MTT assay. To mimic the in vivo setting where non-targeted agents are likely to interact with tumor cells for a relatively short period of time, cells were treated for 30 min with drug-containing medium, followed by continuous culture for another 48 h in drug-free fresh medium. FIG. 9C shows the cytotoxicity in KB cells. FASA was not active in inhibiting the tumor cell proliferation, even at the highest concentration of 200 μg/mL. DOX inhibited the cell proliferation in a dose-dependent manner. PASA/DOX was comparable to free DOX in potency. Coupling of folates to PASA/DOX led to a significant improvement in cytotoxicity and FASA/DOX was more effective than free DOX at several DOX concentrations tested. However, the improvement in cytotoxicity of FASA/DOX was essentially eliminated in the presence of excess amount of free folate, which was consistent with the data of cellular uptake. Similar results were observed in 4T1.2, CT26, MDA-MB-468 and HCT116 tumor cells (FIGS. 9D-G). Yet, the level of improvement in cytotoxicity for FASA/DOX varied among the 4 tumor cell lines tested, likely due to the different expression levels of FR in these cell lines. It was also noticed that PASA/DOX was less active than free DOX in the 4 tumor cell lines, which was consistent with a relatively lower level of cell uptake of PASA/DOX as shown in the cellular uptake study. Similar to the data in KB cells, FASA alone was essentially not active in all the 4 tumor cell lines.

Figure 10:
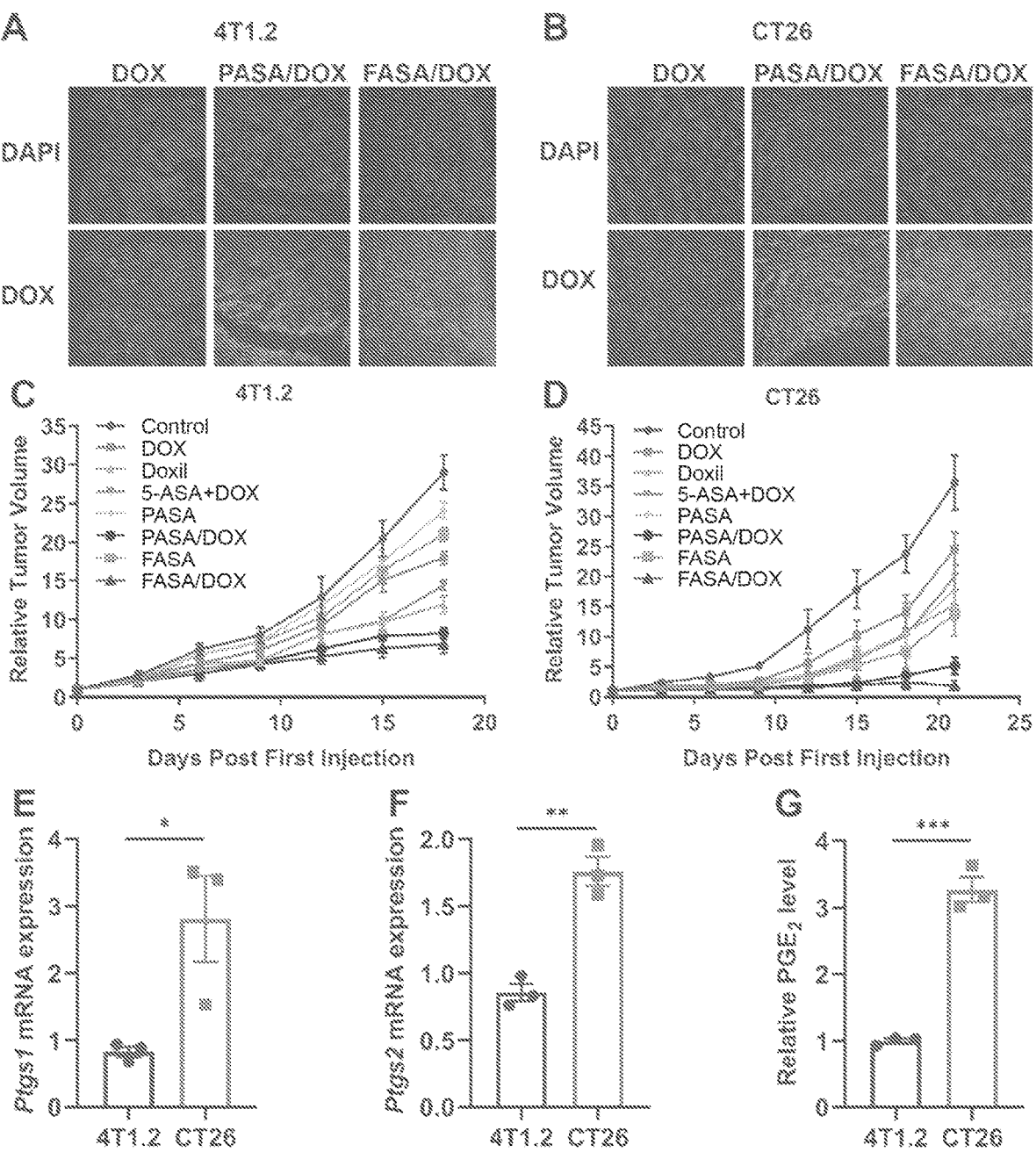
FIG. 10 illustrates biodistribution studies of DOX and in vivo therapeutic efficacy studies in syngeneic murine breast cancer model (4T1.2) and colon cancer model (CT26), wherein panels A-B illustrates fluorescence microscopic examination of DOX distribution in 4T1.2 (panel A) and CT26 (panel B) tumor sections at 24 h after treatment with free DOX, DOX-loaded PASA and FASA micelles, respectively; panels C-D illustrate relative 4T1.2 (C) and CT26 (panel D) tumor volume (n=5) changes of the mice treated with various formulations panels (panel E-G) illustrate ptgs1 mRNA expression and relative $PGE_2$ level (panel G) in 4T1.2 and CT26 untreated tumor tissue (panel E) and ptgs2 mRNA expression and relative $PGE_2$ level (panel G) in 4T1.2 and CT26 untreated tumor tissue (panel F), wherein values reported are the means±SEM, n=3. *p<0.05; p<0.01, *p<0.001.

The biodistribution of DOX in tumors and other major organs was examined following i.v. administration of free DOX, PASA/DOX and FASA/DOX, respectively. Both 4T1.2 and CT26 tumor models (s.c.) were investigated. Tumors and major organs were harvested for fluorescence microscopic examination at 24 h post-injection (FIG. 10, panels A and B). FIG. 10, panel A shows the data from 4T1.2 tumor model. A low level and scattered DOX fluorescence signals were observed in tumor tissues 24 h following a single injection of free DOX. The DOX signals were significantly stronger in PASA/DOX-treated tumors compared to those in free DOX-treated tumors. Incorporation of folate led to a further improvement in DOX accumulation at tumor tissues. In addition to an overall higher level of DOX signals, a more widespread DOX distribution was observed in FASA/DOX-treated tumors. Similar results were observed in CT26 tumor model (FIG. 10, panel B).

For in vivo efficacy study, murine breast cancer 4T1.2 and colon cancer CT26 models were used. When the tumors reached about 50 mm³, mice received different treatments every three days for a total of three treatments on day 0, 3, 6, and tumor volumes were followed every three days. FIG. 10, panel C shows the results in 4T1.2 tumor model. PASA alone slightly inhibited the tumor growth and its antitumor activity was slightly improved following conjugation with folate. Free DOX exhibited a modest antitumor activity and its combination with free 5-ASA led to a slight improvement in efficacy. Doxil, a clinical liposomal DOX formulation, was more effective than the free 5-ASA/DOX combination but less effective compared to DOX formulated in PASA. Decoration of PASA/DOX with folate led to a further improvement in antitumor activity, the most effective one among all treatment groups. In CT26 tumor model (FIG. 10, panel D), a more dramatic antitumor activity was observed for the 5-ASA polymer alone, particularly the folate-conjugated polymer (FASA), its efficacy being similar to that of Doxil. Delivery of DOX via PASA, particularly FASA also led to more effective tumor growth control in CT26 model compared to 4T1.2 tumor model. The data of tumor weights and histopathological analysis of tumor tissues were consistent with the tumor growth curves.

FIG. 10, panels E-G show the mRNA expression levels of Ptgs1/2 genes and the levels of $PGE_2$ in 4T1.2 and CT26 tumor tissues. Consistent with data from cultured tumor cells (FIGS. 6B-D), CT26 tumor tissue showed higher mRNA expression levels of Ptgs1/2 genes and produced greater amounts of $PGE_2$ compared to 4T1.2 tumor tissue. These data, together with the data of in vivo therapy, suggest that Ptgs1/2 may play a more oncogenic role in CT26 model, rendering it more responsive to FASA- or FASA/DOX-based therapy.

In toxicity evaluations, mice treated with free DOX, alone or in combination with 5-ASA experienced a slight decrease in body weights on day 9. The serum levels of AST in the free DOX treated group (DOX or 5-ASA+DOX) were also significantly higher than those in the control group, suggesting a DOX-related hepatotoxicity. Moreover, hepatocellular vacuolation was found in mice treated with free DOX, alone or in combination with 5-ASA. On the other hand, both PASA/DOX and FASA/DOX were well tolerated in mice as manifested with normal body weights and minimal changes in blood levels of AST and ALT, as well as liver and heart histology, suggesting decreased toxicity of DOX following incorporation into 5-ASA-based nanocarrier.

Figures 11A, 11B:
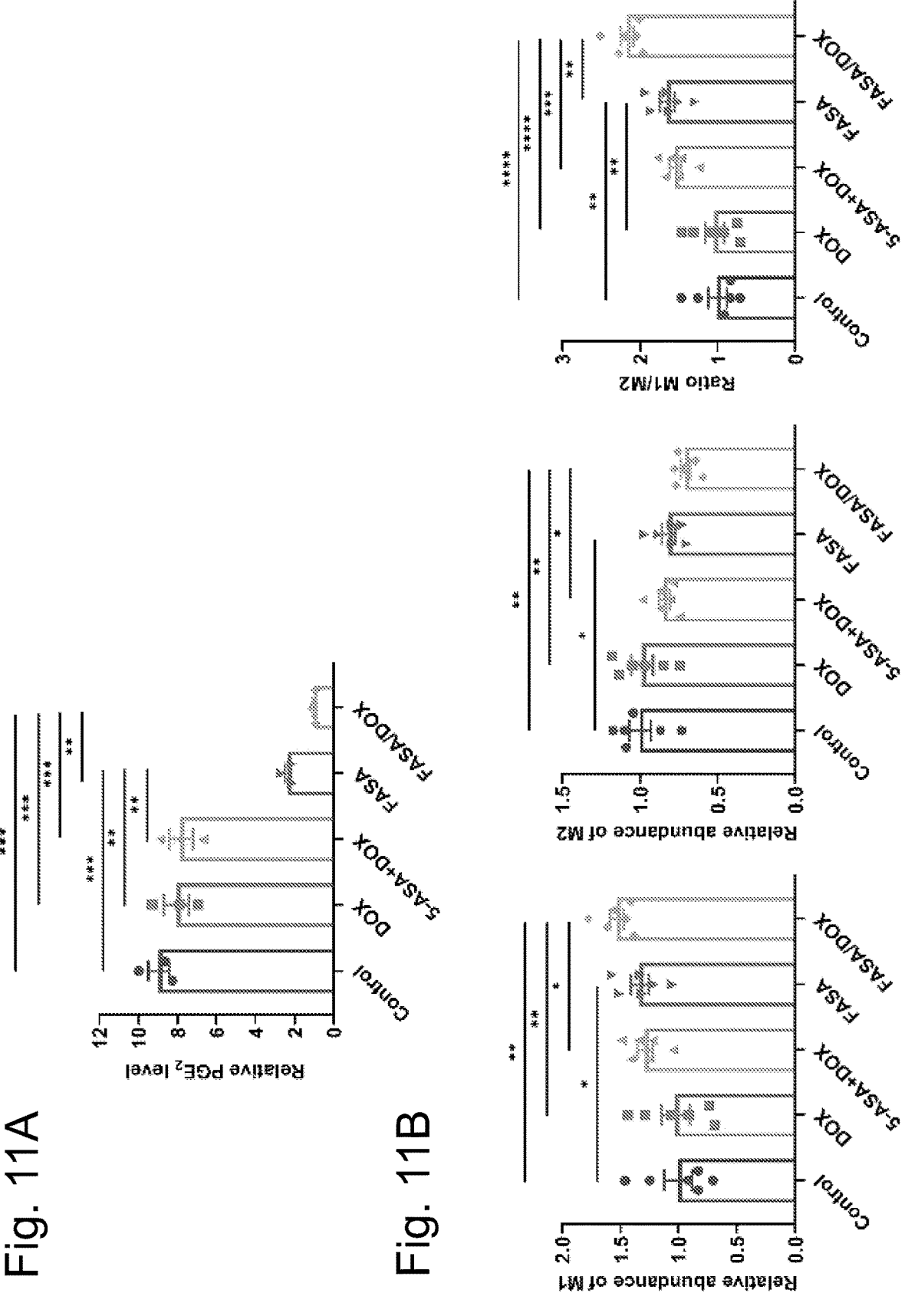
FIG. 11A illustrates $PGE_2$ levels in C126 tumor tissues after different treatments.
FIG. 11B illustrates percentages of TAM population (M1, M2 and M1/M2 ratio) in tumor tissues following different treatments.

The lack of an obvious cytotoxic effect of 5-ASA or PASA in vitro but significant antitumor activity in vivo suggests that 5-ASA or PASA exerts its antitumor activity likely via a mechanism independent of its direct effect on tumor cells. $PGE_2$, a pro-inflammatory cytokine which is produced by COX, gives free rein to cancer immune evasion and immunotherapy resistance. Therefore, the impact of various treatments on the $PGE_2$ production in CT26 tumor tissue was studied. Their impact on tumor immune microenvironment was also investigated. As shown in FIG. 11A, FASA treatment led to a drastic reduction in the level of $PGE_2$ in CT26 tumor tissue while free 5-ASA had minimal effect. Lack of any effect of free 5-ASA is likely due to its rapid elimination and thus limited accumulation at tumor tissue. It is also apparent that codelivery of DOX via FASA resulted in a further decrease in the tissue level of $PGE_2$.

FIG. 11B show that treatment with FASA or FASA/DOX led to downregulation of M2 type macrophages, while M1 type macrophages and M1/M2 ratios were significantly increased, suggesting that the tumor infiltrating macrophages were polarized from a tumor-promoting to a tumor-suppressing phenotype.

Figure 11C:
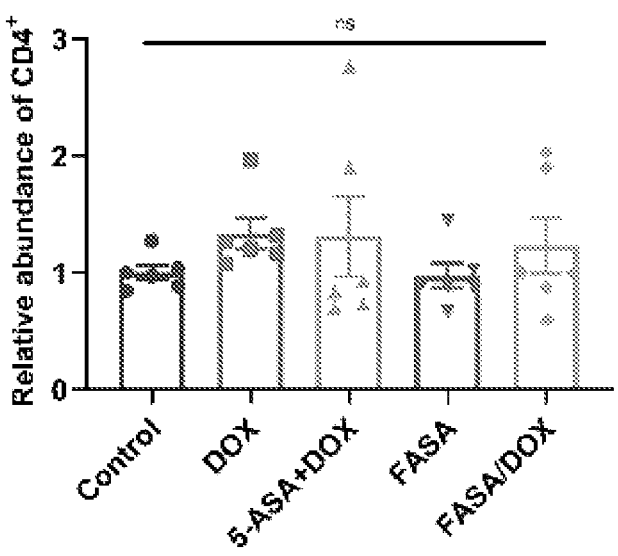
FIG. 11C illustrates relative abundance of CD4$^+$ (upper) and CD8$^+$ (bottom) T cells following different treatments.
Figure 11C:
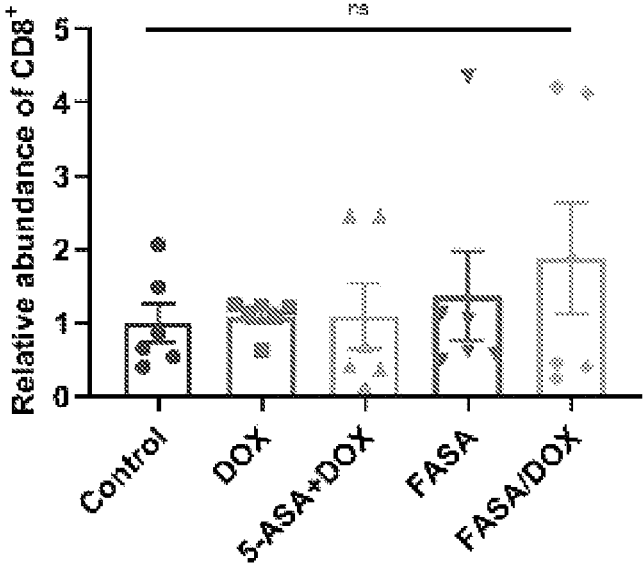
Figure 11D:
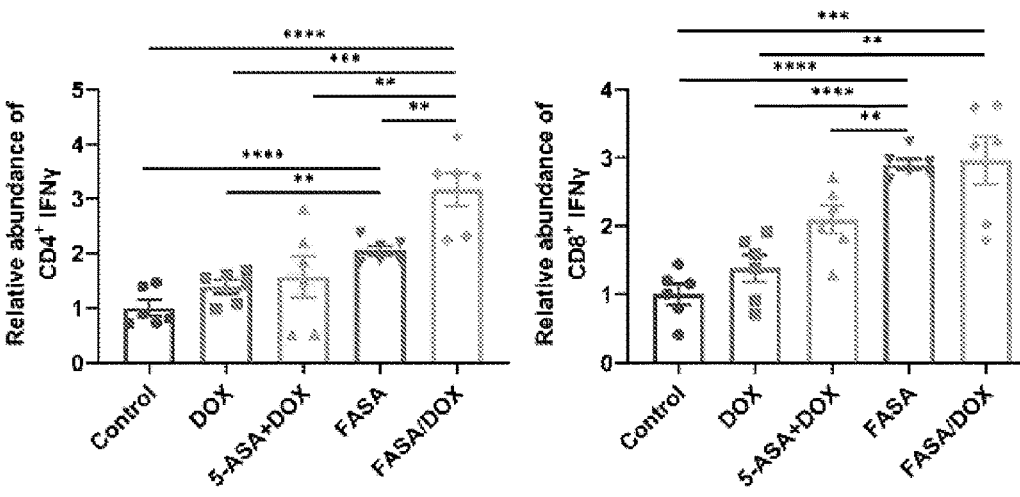
FIG. 11D illustrates IFN-γ$^+$ intratumoral CD4$^+$ and CD8$^+$ T cells following different treatments.
Figure 11E:
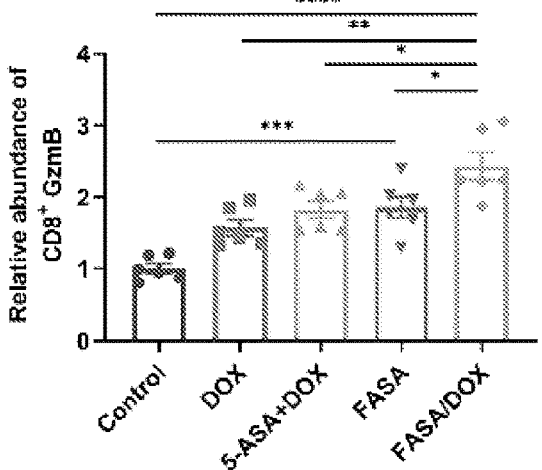
FIG. 11E illustrates granzyme B$^+$ CD8$^+$ T cells following different treatments.

There were minimal changes in the total numbers of $CD4^+$ and $CD8^+$ T cells after the different treatments (FIG. 11C); however, the numbers of IFN-$\gamma^+$ $CD4^+$ and IFN-$\gamma^+$ $CD8^+$ T cells were significantly increased following treatment of FASA or FASA/DOX, particularly the latter treatment (FIG. 11D). IFN-$\gamma$ is a pleiotropic cytokine that can eliminate tumor cells directly and indirectly. Therefore, FASA or FASA/DOX treatment increased the number of functional $CD4^+$ and $CD8^+$ T cells although the total number of $CD4^+$ and $CD8^+$ T cells were not affected. The numbers of GzmB$^+$ $CD8^+$ T cells were also increased following the different treatment, particularly FASA/DOX (FIG. 11E).

Figure 11F:
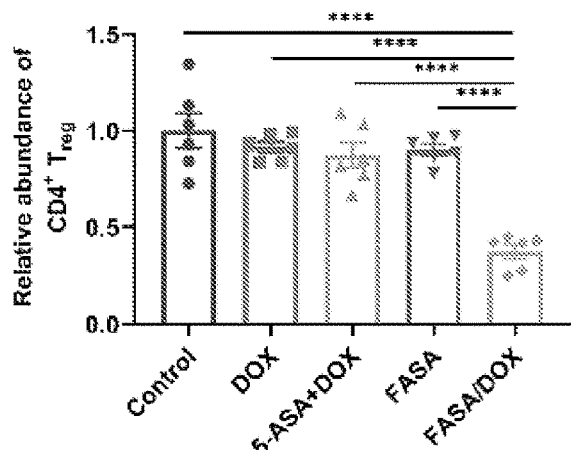
FIG. 11F illustrates FoxP3$^+$ T regulatory cells following different treatments, wherein, in FIGS. 11A through 11F, bars represent means±SEM, and *p<0.05, p<0.01, *p<0.001, ****p<0.0001, ns, no significance.

$T_{reg}$ is immunosuppressive T cell and generally contributes to downregulation of effector T cells. The number of $T_{reg}$ was significantly decreased after treatment with FASA/DOX. However, all other treatments including FASA alone had no impact on the numbers of $T_{reg}$ (FIG. 11F). Overall, a significant improvement in the tumor immune microenvironment following treatment with FASA, particularly FASA/DOX was observed.

Figure 12:
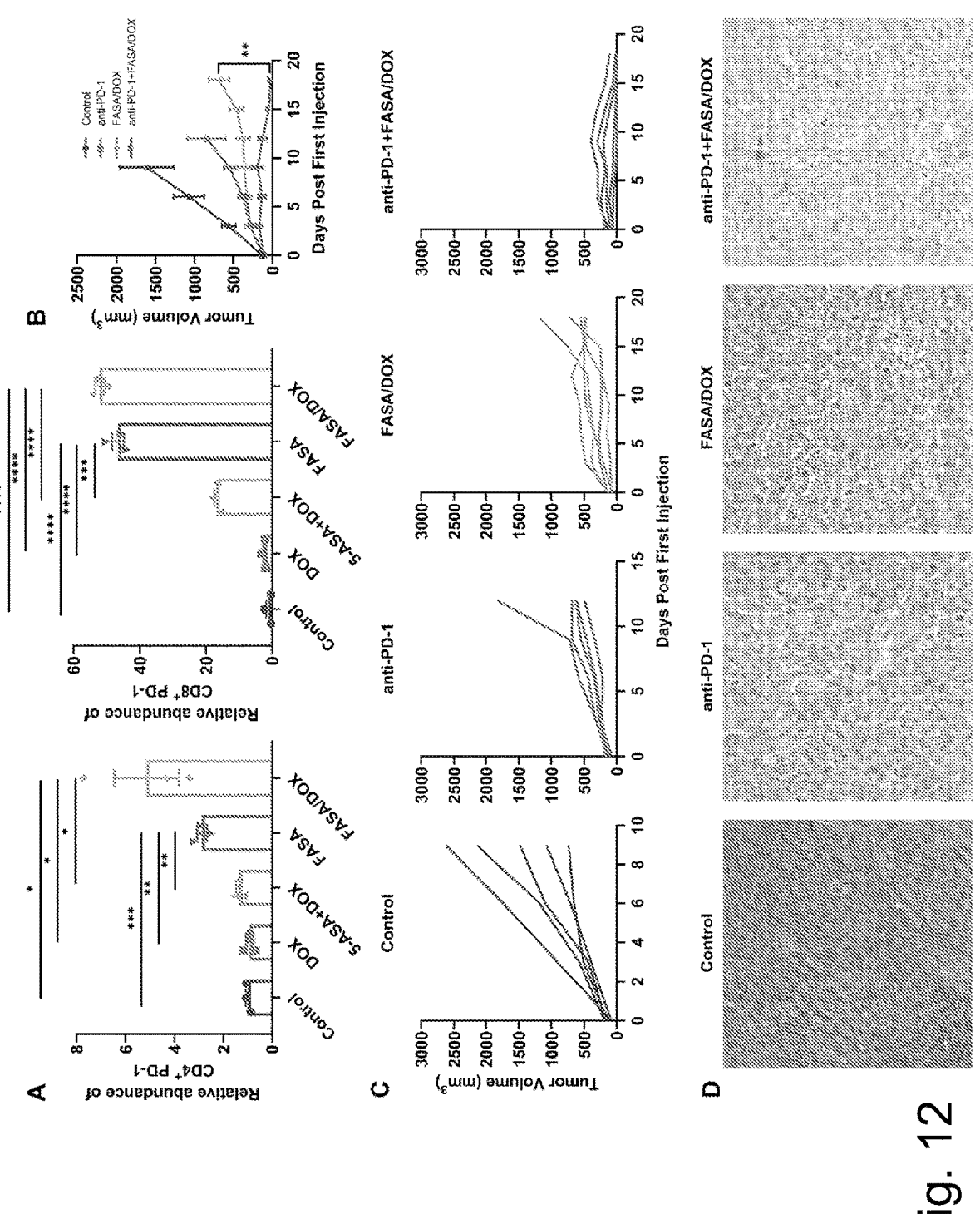
FIG. 12 illustrates in vivo synergistic antitumor activity of PD-1 blockade with FASA/DOX treatment in CT26 tumor model, wherein panel A illustrates percentage of PD-1$^+$ CD4$^+$ and CD8$^+$ T cells in CT26 tumor tissues after treatment, panels B-C illustrate average (panel B) and individual (panel C) tumor growth curves in control and treated group (n=5), wherein all data are means±SEM. *p<0.05, p<0.01, *p<0.001, ****p<0.0001.

Despite many favorable changes in various immune cell subsets as described above, treatment with FASA or FASA/DOX dramatically increased the expression of PD-1 on the surface of $CD4^+$ and $CD8^+$ T cells (FIG. 12, panel A). Upregulation of PD-1 was also observed on $CD8^+$ T cells after treatment with free 5-ASA+DOX combination, although less dramatically compared to treatment with FASA or FASA/DOX. PD-1 is a protein on the surface of cells that prevent the immune system from killing cancer cells. This observation prompted studies of the potential of combining FASA/DOX with anti-PD-1 antibody to further improve the overall therapeutic efficacy. In these studies, treatment was initiated when the tumors reached a relatively large size of 100 mm. In addition, FASA/DOX was given at a reduced DOX dose of 2.5 mg/kg. Anti-PD-1 antibody was given at a dose of 5 mg/kg once every three days for a total of three treatments. As shown in FIG. 12, panel B, anti-PD-1 or FASA/DOX alone showed a modest antitumor activity. Combination of both led to a drastic improvement in the overall therapeutic efficacy. The growth of tumors was well controlled following the 1$^{st}$ treatment. In addition, 4 out of 5 tumors completely regressed at day 18 following the 1$^{st}$ treatment, clearly demonstrating the therapeutic benefit of combining the two treatments (FIG. 12, panel C). The histological analysis showed large nuclei in the tumor tissue with saline treatment, while shrunk nuclei were observed in the tumor tissues with other treatments, especially combination group (FIG. 12, panel C). All treatments were well tolerated as manifested by minimal changes in body weights and blood levels of AST and ALT, as well as normal histological morphology, indicating negligible toxicity of combination FASA/DOX with anti-PD-1 treatment.

Figure 13:
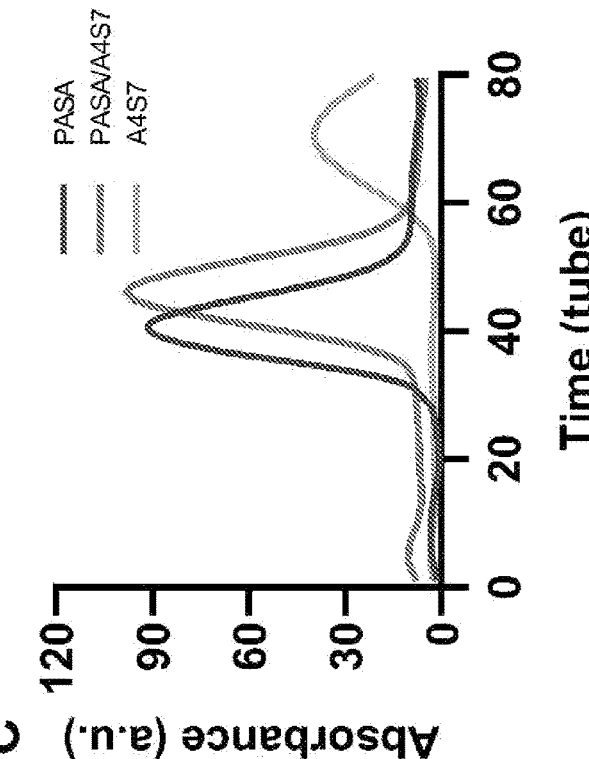
FIG. 13A illustrates zeta potential characterizations of a PASA polymer hereof and A4S7 peptide.
FIG. 13B illustrates size distribution characterization of blank PASA polymer hereof and PASA/A4S7 micelles at a carrier/peptide ratio 5/1 (mg/mg).
FIG. 13C illustrates UV/Vis absorbance spectra of DOX, PASA/DOX and PASA in aqueous solution wherein the carrier/drug ratio was at 5/1 (mg/mg).
Figure 13:
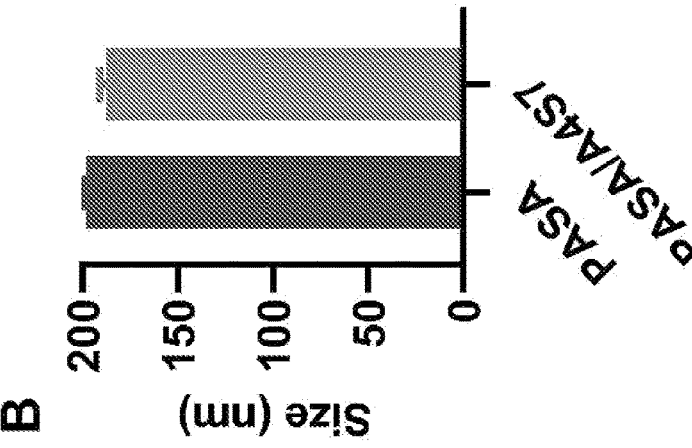
Figure 13:
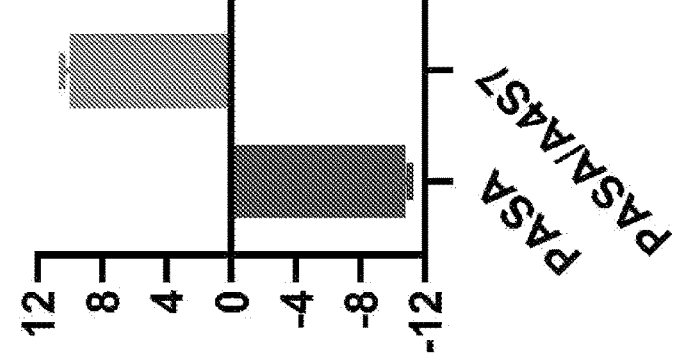

The polymer-based nanocarriers hereof may be used as carriers for a wide variety of molecules/drugs. FIG. 13, for example, illustrates several studies of a PASA-based nanocarrier for peptide delivery. As described above, amphiphilic polymer, PASA, self-assembles to form nanoparticles (NPs) in aqueous solution. Studies with A4S7 (a cationic antimicrobial peptide) showed that PASA was highly effective in loading cationic peptides through various mechanisms of carrier/peptide interactions including strong ionic interaction, $\pi$-$\pi$ stacking and hydrophobic interaction, leading to the formation of a more compact structure. As shown in FIG. 13, panel A, PASA showed negative zeta potential, which can be reversed by loading A4S7 cationic peptides. The size of blank PASA is around 197.5 nm (see FIG. 13, panel B). Incorporation of A4S7 into PASA NPs resulted in slight decreases in sizes (193.5 nm). G-50 gel filtration profile showed well-separated PASA/A4S7 from free A4S7 (FIG. 13, panel C), indicating that all input A457 was loaded into PASA NPs. The significantly increased retention time of PASA/A4S7 compared to PASA suggests the formation of more compact NPs. The system has the advantages of simplicity and high-loading capacity and can be broadly applicable for delivery of, for example, cationic peptides of different sequences.

FIG. 14 illustrates Table 2 setting forth studies of micelle size for formulation hereof including PASA/Imatinib (a tyrosine kinase receptor inhibitor) and FASA/Cisplatin (a platinum-based antineoplastic medication) of various ratios.

The polymer-based nanocarriers hereof were also used in formulating a representative combination therapy for treatment of CRC. Cancer of the colon and rectum (CRC) is one of the most prevalent tumors worldwide, especially in the economically developed regions. CRC, with an annual cases of over 1.93 million (2020), is the third most common incidence (following lung and breast cancers) and the second cause of cancer mortality worldwide. Approximately 8-15% of all CRC patients harbor activating mutations (mostly V600E mutation) of BRAF. Among subtypes of CRC, BRAF-mutated CRCs are less responsive to chemotherapy, do not benefit from anti-EGFR (Epidermal Growth Factor Receptor) therapy, and had the highest mortality. Tremendous effort has been put forth to develop effective strategies to overcome BRAF resistance, but thwarting resistance to BRAF inhibitors remains one of the major clinical challenge in therapy against CRC.

Recently various combination therapies are under preclinical and clinical evaluations for the treatment of BRAF-mt CRC. A phase I/II trial combining the inhibition of BRAF (dabrafenib) and MEK (trametinib) in 43 BRAF V600-mutant CRC patients showed that 12% of the patients achieved a partial response, or better, lasting over 36 months. Moreover, 56% of the patients achieved stable disease. The study supports that a subset of patients with BRAF V600-mt CRC could benefit from a combined dabrafenib/trametinib therapy. Other combination therapies include those co-targeting EGFR/BRAF, EGFR/BRAF/ MEK, EGFR/BRAF/PI3K, and BRAF/MEK/PI3K. One concern with the combination therapy, particularly the triple combination therapy, is the added toxicity.

As described above, various combination therapies are under preclinical and clinical evaluations for the treatment of BRAF-mt CRC. Enhanced codelivery using a nanocarrier will not only decrease the toxicity but also improve the therapeutic efficacy. In a number of embodiments hereof, an improved combination therapy co-targeting BRAF/MEK/ PI3K that is based on codelivery of dabrafenib, trametinib, and alpelisib (DTA) is provided through a novel immunostimulatory nanocarrier hereof.

Prostaglandin E2 ($PGE_2$), produced by Cyclooxygenase (COX)-1 and 2, plays a predominant role in promoting inflammation and tumor progression by regulating downstream targets which control cell proliferation, angiogenesis, and immunosuppression. Emerging evidence indicates that upregulation of the RAF-MAPK pathway by BRAF mutation may activate PTGS2 (COX-2) in tumor cells to increase the production of $PGE_2$. There is a stronger association of tumor PTGS2 (COX-2) expression with colorectal cancer mortality in BRAF-mutated tumors than in BRAF-wild-type tumors. In a number of embodiments hereof, a PASA prodrug-based polymeric carrier was studied for codelivery of 5-ASA, dabrafenib, trametinib, and alpelisib.

Figure 15A:
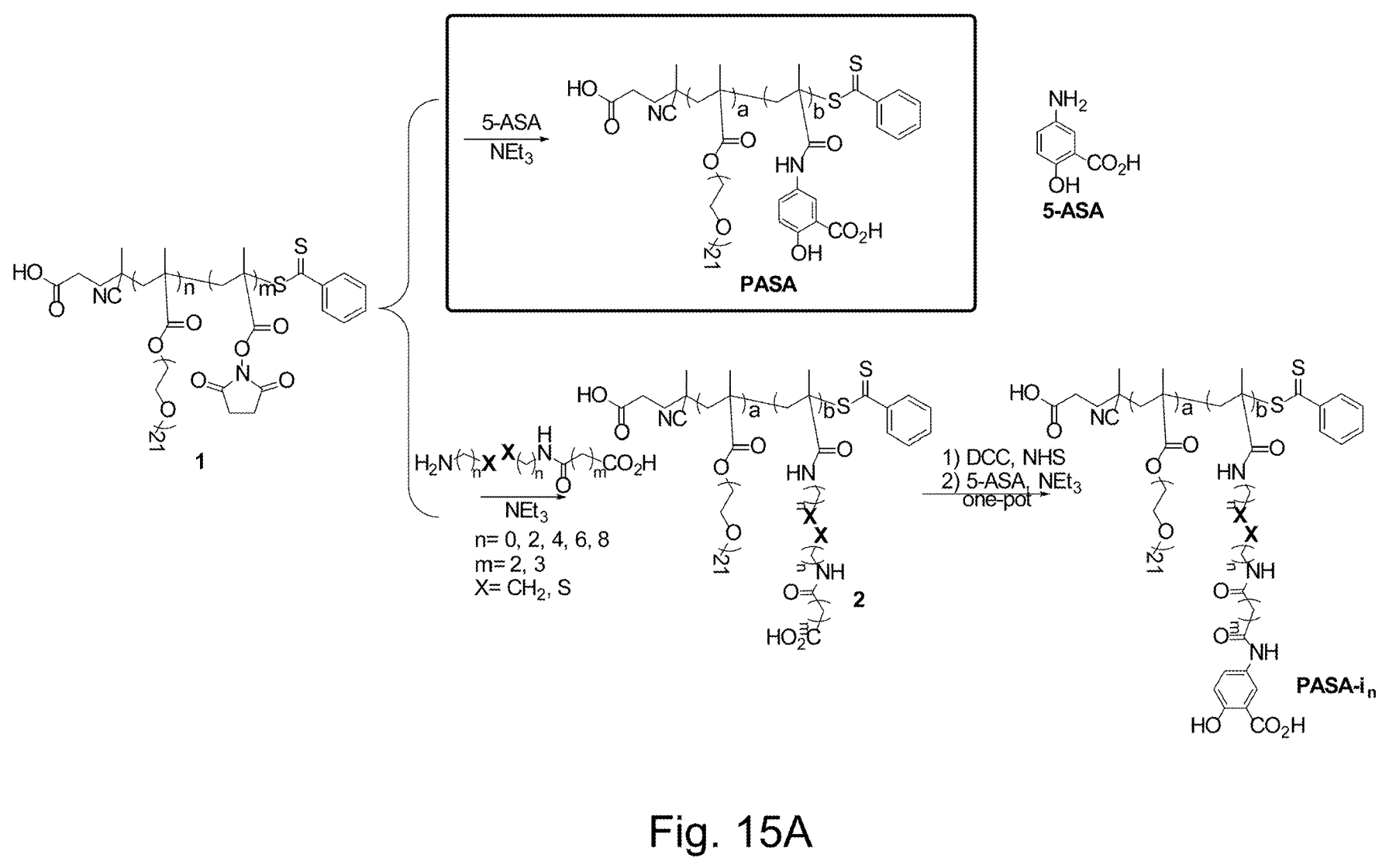

To synthesize the PASA polymer as described above, the 5-ASA was used to conjugate with a PEG-b-PNHS backbone (compound 1) directly to form amide bond as illustrated in FIG. 15A. Such PASA polymers include a short linker between 5-ASA and polymer backbone. Such polymers formed blank micelles of relatively large size (197.6 nm) as described above. To obtain small NPs, which may, for example, be coloaded with DTA, in another embodiment of PASA polymer (sometimes referred to herein as PASA-i) was synthesized through introducing a longer alkyl spacer between the polymer backbone and 5-ASA (FIG. 15A). First, the bifunctional linker was synthesized which was subsequently conjugated to PEG-b-PNHS. Second, the carboxyl acid (compound 2) was converted to NHS ester followed by conjugation with 5-ASA through amide bond (PASA-i$_n$).

Figure 15B:
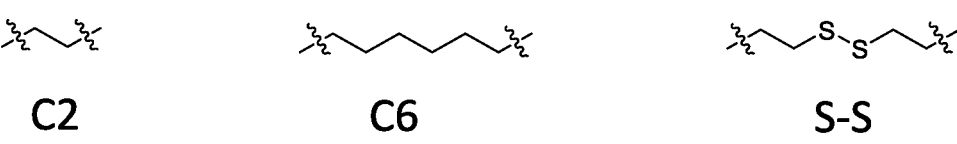
FIG. 15B illustrates representative linking moieties via which the first therapeutic compound (for example, a COX inhibitor) inhibitor may be attached to a polymer hereof.
Figures 16A, 16B, 16C:
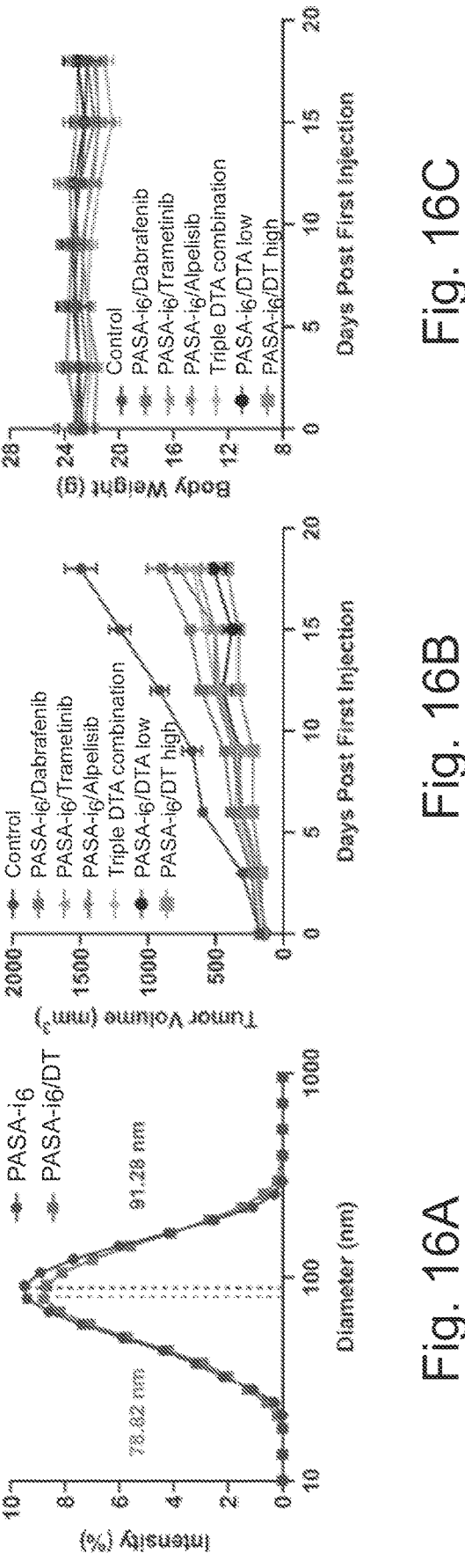
FIG. 16A illustrates size distribution of blank PASA and PASA/DTA micelles for the PASA polymer of FIG. 15A.
FIG. 16B illustrates changes in tumor volume in WiDr tumor bearing NSG mice receiving different treatments including combination therapies using the PASA polymer of FIG. 15A.
FIG. 16C illustrates changes in body weight in WiDr tumor bearing NSG mice receiving different treatments including combination therapies using the PASA polymer of FIG. 15A.

Without limitation to any mechanism, it is postulated that inclusion of a longer, hydrophobic spacer group or linking moiety ($L^1$), assists in forming a more compact micellar core through enhanced hydrophobic interaction. Linking moiety ($L^1$) may, for example, interact with the second therapeutic compound via hydrophobic interaction, hydrophilic interaction, and/or π-π stacking. Representative example of interactive linking moieties ($L^1$) or groups therefore are illustrated in FIG. 15B. PASA-i$_6$ is a new PASA analogue with 6 carbons between polymer backbone and 5-ASA. PASA-i$_6$ formed blank micelles of significantly reduced size (91.28 nm) compared to PASA. Using a microfluidic system, DTA could be co-loaded into PASA-i$_6$ with the size of NPs being 78.82 nm. The microfluidic system included a microfluid injection pump. Each of dabrafenib, trametinib and alpelisib was dissolved in ethanol. The resultant drug-containing solution was injected into stirred PASA solution through the microfluid injection pump. Preliminary studies indicated that codelivery of DTA via PASA-i$_6$ led to significant inhibition of tumor growth in a human BRAF-mt CRC model (WiDr). Mice were treated with various formulations every three days in the timeframe of a week (day 0, 3, 6, 9, 12). The effect of the treatments was followed up every three days by tumor volume measurement. PASA-i$_6$/DTA treatment is much more effective than free DTA combination or PASA-i$_6$ loaded with each single drug (FIG. 16B). Mice treated with free DTA combination experienced a slight decrease in body weights on day 15. On the other hand, PASA-i$_6$/DTA of both low dose and high dose were well tolerated in mice as manifested by normal body weights (FIG. 16C).

Figure 17A:
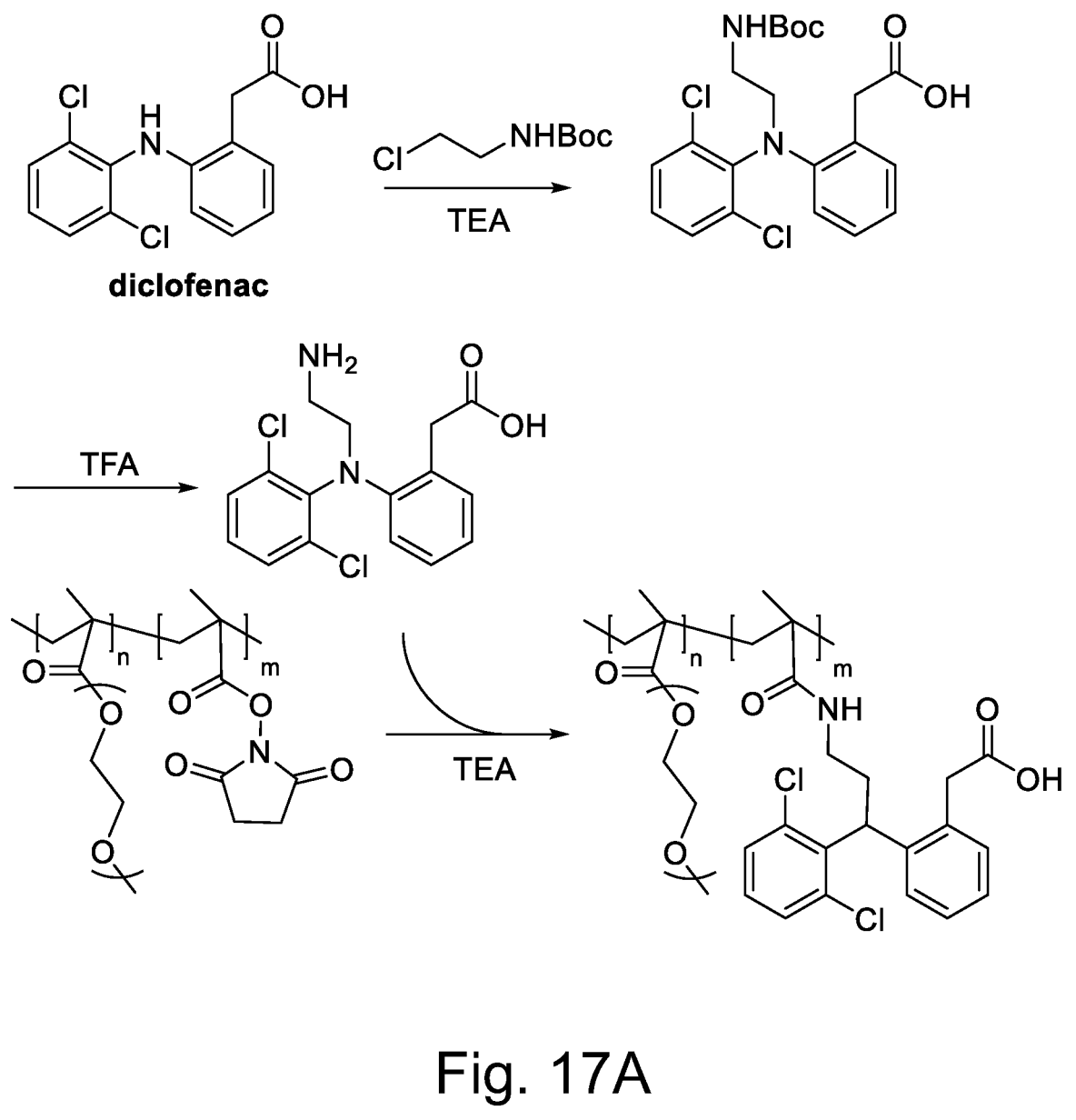
Figure 17B:
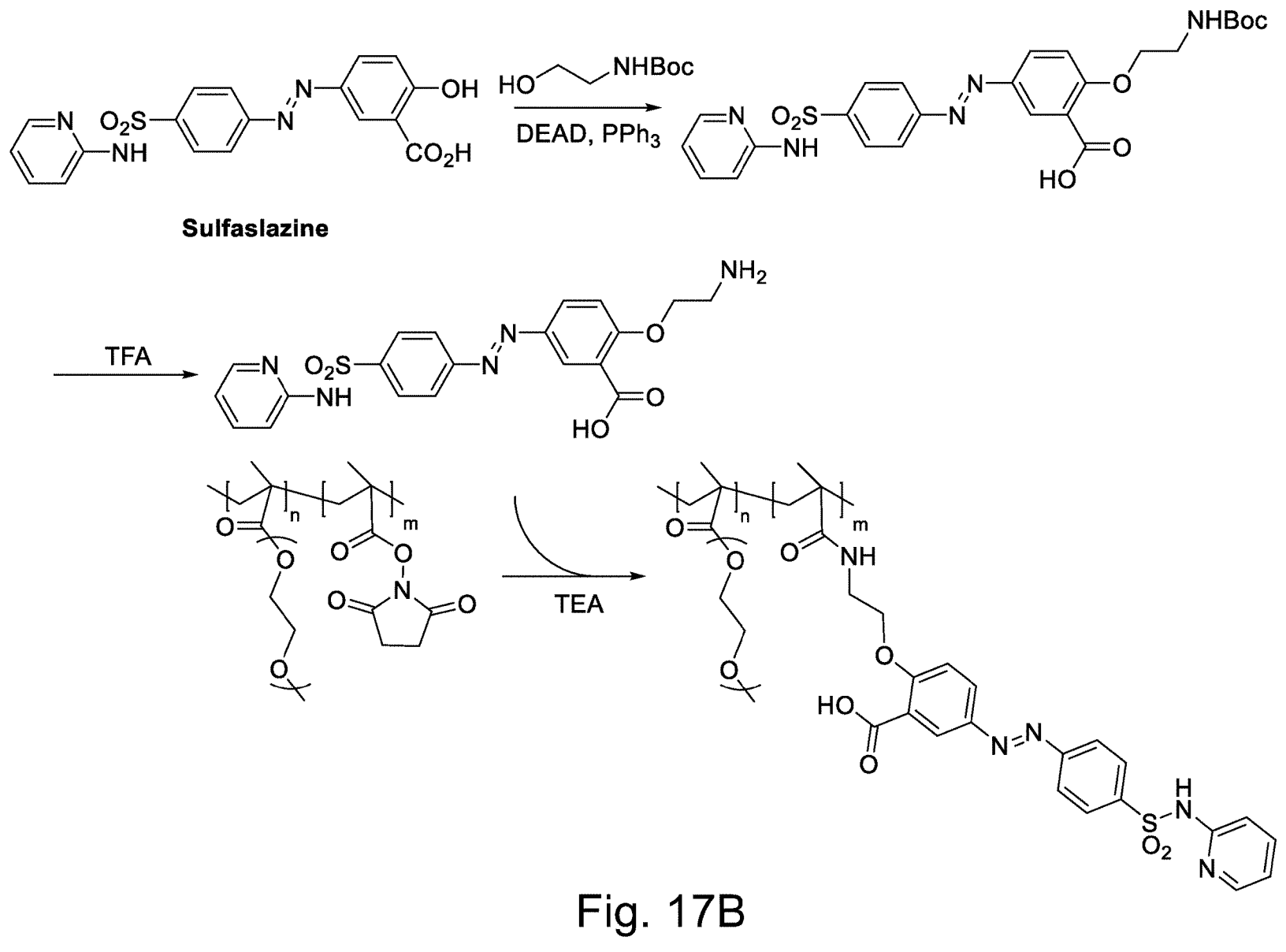

As described above, pendant group (X) is, in a number of embodiments hereof, is a residue of a first therapeutic compound such as a COX inhibitor which is reacted (via a functional group on the first therapeutic compound; either directly or through one or more intermediate reactions) with a functional group on the polymer to attached (X) via a labile bond (thereby forming a prodrug). In the representative embodiments described above, pendant group (X) includes a residue of 5-ASA. FIGS. 17A and 17B illustrate, respectively, representative synthetis schemes for incorporating residues of the representative COX inhibitors diclofenac and sulfasalazine into pendant groups on the polymers hereof.

COX has been well studied in terms of its role in tumorigenesis and progression including its impact on tumor immune microenvironment. However, a role of tumor-derived COX in COX inhibitors-mediated antitumor activity has not been well elucidated. Many studies used COX inhibitors at concentrations that are significantly higher than the effective concentration required to inhibit $PGE_2$ synthesis. The studies hereof showed that 5-ASA, at concentrations effective in inhibiting $PGE_2$ synthesis, showed minimal cytotoxicity on several human and murine cancer cell lines with varying levels of COX. To the contrary, 5-ASA showed significant tumor growth inhibition on two murine cancer models, 4T1.2 and CT26, particularly upon improved delivery of 5-ASA using a 5-ASA polymer-based prodrug (see FIG. 10). In addition, a more drastic effect was observed in CT26 tumor model that has a higher level of COX expression. The data suggest that 5-ASA largely inhibits the tumor growth in vivo via a mechanism that is independent of direct effect on tumor cell proliferation. The fact that CT26 responded more dramatically to 5-ASA treatment suggests that COX might play a more oncogenic role in CT26 tumor compared to 4T1.2 tumor model, which is consistent with previous clinical research that NSAIDs reduce the risk of colorectal cancers that overexpress COX2 but have minimal impact on the colorectal cancers with weak expression of COX2. It is possible that mechanisms other than COX inhibition also contribute to the different responses to 5-ASA treatment between the two tumor models.

5-ASA treatment led to an improvement in the tumor immune microenvironment (see FIGS. 11A-F). It has been reported that $PGE_2$ secreted by tumor cells is one of the principal mediators allowing tumor cells to escape immunosurveillance. $PGE_2$ was shown to induce differentiation of macrophages from an M1 to an M2 phenotype and the production of pro-inflammatory factors, such as CXCL1 and IL-6. Accordingly, myeloid cells could be stimulated by $PGE_2$ secreted from mouse melanoma tumor cells to produce CXCL1, IL-6 and G-CSF[3]. Moreover, $PGE_2$ potently suppressed NK cell activity, which could be recovered by depletion of tumor-derived $PGE_2$. FIGS. 11A-F show that 5-ASA treatment was associated with increases in M1/M2 ratio and the number of functional $CD4^+$ and $CD8^+$ cells. The data hereof are consistent with the published literature. The data hereof also show that combination of 5-ASA and DOX resulted in a further improvement in tumor immune microenvironment. In addition to direct killing of tumor cells, DOX can elicit antitumor immunity through induction of immunogenic cell death. 5-ASA that was slowly released from the 5-ASA polymer helped to further improve and sustain an active tumor immune microenvironment.

The representative PASA polymer hereof was designed based on 5-ASA structure to facilitate codelivery of 5-ASA and, for example, DOX. Amino group in the 5-ASA structure rendered it easy to conjugate to the polymer to form a prodrug. As a 5-ASA polymer-based prodrug, PASA could slowly release 5-ASA over a prolonged period to achieve sustained inhibition of COX. In addition, PASA could self-assemble to form a micellar carrier to co-deliver another drug such as DOX. Many carriers have been reported for delivery of DOX or codelivery of DOX and another drug. A significant advantage of the nanocarriers hereof lies in the unprecedented high DOX loading capacity (42.28%) (Table 1 of FIG. 8E). This may, for example, be attributed to a strong carrier/drug interaction as a result of multiple mechanisms of PASA/DOX interaction including ionic interaction as well as hydrophobic/hydrophobic and π-π interactions. These strong interactions led to the formation of highly compact nanoparticles as evidenced by the significantly reduced particle size following incorporation of DOX into PASA micelles (197.6 nm vs. 67.9 nm). These strong PASA/DOX interactions may also explain a very slow kinetics of DOX release from DOX-loaded PASA micelles compared to many reported DOX micellar formulations. The excellent stability of DOX-loaded micelles together with their small sizes (~70 nm) contributed significantly to the effective accumulation of DOX after systemic administration.

Delivery of DOX via PASA led to a significant improvement in antitumor activity over free 5-ASA/DOX combination or Doxil, a clinical liposomal DOX formulation. The improved therapeutic efficacy of PASA/DOX may be largely attributed to the enhanced delivery of 5-ASA and DOX to tumor tissues. As discussed above, the synergistic action between the two in improving the immune microenvironment, may also play a role. A further improvement in antitumor activity was observed for both PASA and PASA/DOX following conjugation with folate. Folate receptor, particularly FRα, has been reported to be overexpressed in various types of human and murine cancers. In addition, tumor macrophages, particularly M2 macrophages overexpress FR, mainly FRβ. Data of confocal laser scanning microscopy (CLSM) studies hereof of M2 macrophages after incubation with free DOX, PASA/DOX, PASA/DOX with free folate, FASA/DOX, and FASA/DOX with free folate for 30 minutes (wherein DOX concentration was at 6

µg/mL, and free folate was at 100 µM) suggest that folate ligand can facilitate cellular uptake of FASA polymer by M2 macrophages. Thus, the enhanced antitumor activity of FASA or FASA/DOX may benefit from targeting of both tumor cells and macrophages, particularly considering that tumor M2 macrophages also express a high level of COX-2.

Expression levels of PD-1 on $CD4^+$ and $CD8^+$ cells were significantly upregulated following treatment with free 5-ASA/DOX combination, FASA, and FASA/DOX, respectively, particularly the latter two treatments (FIG. 12). Upregulation of PD-1 could be secondary to the increased production of IFN-γ as a result of an enhanced antitumor immunity. However, a role of tumor-derived $PGE_2$ in regulating the expression of PD-1 on immune cells was suggested by a previous study showing a high expression level of PD-1 in COX knockout tumors. Nonetheless, the results hereof pointed to a potential combination of FASA/DOX with anti-PD-1 antibody. Indeed, a significant improvement in the overall antitumor activity was observed for the combination therapy including complete regression of some established tumors at a suboptimal dose of FASA/DOX.

In summary, tumor-derived COX plays an important role in promoting an immunosuppressive tumor microenvironment. The dual functional nanocarriers hereof are highly effective in codelivery of 5-ASA, a representative COX inhibitor, and various therapeutic compounds. Delivery of chemotherapeutic agents via nanocarriers hereof, either alone or in combination with, for example, immune checkpoint blockade, may hold promise as a new and effective immunochemotherapy for various types of cancers, particularly those COX-overexpressing cancers.

Experimental

Reagents. 5-ASA was purchased from Frontier Scientific (UT, U.S.A). DOX·HCl was purchased from LC Laboratories (MA, U.S.A). 4-Cyano-4 [(dodecylsulfanylthiocarbonyl)sulfanyl] pentanoic acid, 2-Azobis-(isobutyronitrile) (AIBN), poly(ethylene glycol) methacrylate (average Mn=950, $PEG_{950}$), 3-(4,5-dimethylthiazol-2-yl)-2,5-diphenyl tetrazolium bromide (MTT), Dulbecco's Modified Eagle's Medium (DMEM) and folic acid were purchased from Sigma-Aldrich (MO, U.S.A). AIBN was purified by recrystallization in anhydrous ethanol. N-Succinimidyl Methacrylate was purchased from TCI (U.S.A). RPMI-1640 medium and folate-deficient RPMI-1640 medium, fetal bovine serum (FBS) and penicillin-streptomycin solution were purchased from Invitrogen (NY, U.S.A). All solvents used in this study were HPLC grade.

Cell culture. All cell lines used in this work were obtained from ATCC (Manassas, VA). 4T1.2 murine triple negative breast cancer cells and MDA-MB-468 human triple negative breast cancer cells were cultured in DMEM. CT26 murine colon cancer cells and HCT116 human colon cancer cells were maintained in RPMI-1640 medium. KB human epidermoid carcinoma cells were culture in FA-deficient RPMI-1640 medium. All cells were cultured at 37° C. in a humidified atmosphere with 5% $CO_2$. All media were supplemented with 10% fetal bovine serum (FBS) and 1% penicillin-streptomycin.

Animals. Female BALB/c mice (4-6 weeks) were purchased from The Jackson Laboratory (ME, U.S.A). All animals were housed under pathogen free conditions according to AAALAC (Association for Assessment and Accreditation of Laboratory Animal Care) guidelines. All animal-related experiments were performed in full compliance with institutional guidelines and approved by the Animal Use and Care Administrative Advisory Committee at the University of Pittsburgh.

Real-Time PCR. cDNA was generated from the purified RNA extracted from cultured cells or tumor tissues using QuantiTect Reverse Transcription Kit (Qiagen, MD, U.S.A) according to the manufacturer's instructions. Quantitative real-time PCR was performed using SYBR Green Mix on a 7900HT Fast Realtime PCR System. Relative target mRNA levels were analyzed using delta-delta-Ct calculations and normalized to GAPDH.

Synthesis of PEG-b-PNHS polymer. 4-Cyano-4-(thiobenzoylthio) pentanoic acid (10.2 mg, 0.0366 mmol), AIBN (2 mg, 0.0124 mmol), N-Succinimidyl methacrylate (430 mg, 2.42 mmol), PEG$_{950}$ (356 mg, 0.375 mmol), and 2 mL of dried tetrahydrofuran were added into a Schlenk tube. Then the mixture was filled with N$_2$ and stirred at 80° C. for overnight. The reaction was quenched, and the mixture was precipitated in ethanol once and diethyl ether twice, separately. PEG-b-PNHS was collected as precipitate and dried. Conversion of PEG$_{950}$ polymer was 76% and the conversion of N-Succinimidyl methacrylate was 97%.

Synthesis of PASA polymer. PEG-b-PNHS (303 mg, 1 mmol NHS), 5-ASA (459 mg, 3 mmol) and TEA (416.2 μL, 3 mmol) were dissolved in DMSO (10 mL) and stirred at 37° C. After 48 h reaction, the mixture was dialyzed against DMSO for two days, followed by dialysis against water for three days. The PASA polymer was obtained after lyophilization.

Synthesis of FASA polymer. The PEG$_{3.5K}$-FA was first synthesized according to a previously published method[18]. PEG$_{3.5K}$-FA (78 mg, 0.02 mmol), PEG-b-PNHS (303 mg, 1 mmol NHS), and TEA (27.5 μL, 0.1 mmol) were then dissolved in DMSO (10 mL) and stirred at 37° C. for 48 h. Then 5-ASA (459 mg, 3 mmol) and TEA (416.2 μL, 3 mmol) were added and the reaction mixture was stirred for another 48 h. The mixture was dialyzed against DMSO for two days, followed by dialysis against water for three days. The FASA polymer was obtained after lyophilization.

Chemical characterization of synthesized polymer. $^1$H-NMR spectrum of synthesized polymer was examined on a Varian-400 FT-NMR spectrometer at 400.0 MHz with DMSO-d$_6$ as the solvent.

Preparation and physiochemical characterization of blank or drug-loaded micelles. Blank and DOX-loaded micelles were prepared by film hydration method. DOX solution (5 mg/mL) was first prepared by dissolving DOX in a mixture of dichloromethane/methanol (1:1, v/v) containing triethylamine (5 equiv.). Then DOX solution was mixed with the PASA or FASA polymer (5 mg/mL in dichloromethane) at different polymer/drug weight ratios. The solvent was removed by nitrogen flow, followed by 2 h in vacuum to further remove remaining solvent. The thin film formed was hydrated in 0.1 M PBS to give DOX-loaded micelles. The size distribution of prepared micelles was measured via dynamic light scattering (DLS) method. The morphology of blank and drug-loaded micelles was observed by transmission electron microscopy (TEM). DOX concentrations in micelles were determined by Waters Alliance 2695 Separations Module combined with Waters 2475 Fluorescence Detector (excitation, 480 nm; emission, 510 to 620 nm; gain, 3; sensitivity (FUFS), 10,000), and drug loading capacity (DLC) and drug loading efficiency (DLE) of DOX were calculated according to the following equations: DLC (%)= [weight of loaded drug/(weight of polymer+input drug)]× 100%, DLE (%)=(weight of loaded drug/weight of input drug)×100%. The colloidal stability of micelles was monitored at room temperature by following the changes in sizes of the particles or visible precipitates every hour in the first 12 h and daily after 12 h following sample preparation. The absorbance spectra of DOX, PASA and PASA/DOX were collected using a Varian 50 Bio UV-Vis spectrophotometer.

Critical micelle concentration (CMC) of 5-ASA polymer-based micelles. The CMC of PASA and FASA polymer was determined by fluorescence measurement using nile red as a fluorescence probe as described previously[19]. Briefly, nile red dichloromethane solution (0.05 mg/mL) was added to the test tubes and then the solvent was removed by evaporation at room temperature. Then, 2 mL of PASA or FASA micelles ranging from $1\times10^{-4}$ to $5\times10^{-1}$ mg/mL was added to each tube with nile red respectively. The micelles were kept overnight to allow the solubilization equilibrium of nile red. Excitation was carried out at 550 nm with emission recorded from 570 to 720 nm wavelength.

Gel Retardation Assay. PASA/DOX micelles of different weight ratios (ranging from 1:1 to 20:1; DOX concentration was fixed at 0.5 mg/mL) were prepared at different pH (7.4 or 5) by film hydration method as mentioned above. These micelles were electrophoresed on agarose gel in Tris-acetate-EDTA (TAE) buffer of corresponding pH. Gel electrophoresis was carried out at 120 V for 20 min and the gel was subsequently visualized using a UV illuminator. Free DOX was used as a control.

In vitro drug release. The release of DOX from DOX-loaded PASA and FASA micelles at different pH was studied using a dialysis method. Briefly, 2 mL of PASA/DOX and FASA/DOX micelles containing 1 mg of DOX and 10 mg of polymer were placed in a dialysis bag (MWCO 3.5 kDa) and immersed into 40 mL of 0.1 M PBS solution containing 0.5% (w/v) Tween 80 at pH 5 and pH 7.4. The experiment was performed in an incubation shaker at 37° C. at 100 rpm. At selected time intervals, 10 μL solution in the dialysis bag and 1 mL medium outside the dialysis bag were withdrawn while same amount of fresh dialysis solution was added for replenishment. The concentration of DOX was examined by fluorescence spectrometry (excitation, 480 nm; emission, 510 to 620 nm). Free DOX was included as control.

Cellular uptake study. KB, 4T1.2, CT26, MDA-MB-468, HCT116 tumor cells and M2 macrophages were seeded to 6-well plates ($3\times10^5$/well), respectively. After overnight incubation, the culture medium was replaced by fresh medium containing free DOX, PASA/DOX and FASA/DOX micelles with or without 100 μM free folate, respectively, at an equivalent DOX concentration of 6 μg/mL (carrier/DOX ratio: 10/1 (w/w)). After incubation for 30 min at 37° C., cells were washed with cold PBS and fixed with PBS containing 4% (w/v) formaldehyde. Nuclei were then stained by DAPI for 5 min. Cells were washed with cold PBS and observed under fluorescence microscope (BZ-X710, Japan).

Cellular uptake of different DOX formulations was also quantified by flow cytometry. KB tumor cells seeded in 6-well plates ($3\times10^5$/well) were treated with various DOX formulations as described above at a DOX concentration of 6 μg/mL. Following incubation at 37° C. for 30 min, cells were washed with cold PBS, fixed in PBS containing 4% (w/v) formaldehyde, and resuspended in 500 μL PBS for flow cytometry analysis with CyAn ADP Analyzer (Beckman Coulter, Inc.). Fluorescence was examined at an excitation wavelength of 480 nm and an emission wavelength of 570 nm. $2\times10^4$ events were collected for each sample.

In vitro cytotoxicity. Cytotoxicity assay was performed on different cancer cell lines (KB, 4T1.2, CT26, MDA-MB-468 and HCT116). Cells were seeded in 96-well plates at a density of $5\times10^3$ cells/well with 100 μL of complete culture medium (DMEM or RPMI 1640 with 10% FBS and 1% streptomycin/penicillin).

To evaluate the combination effect of 5-ASA and DOX, cells were treated with various concentrations of free 5-ASA, DOX and the combination, and MTT assay was performed 48 h later. The absorbances of each well were measured at 590 nm and the cell viability was determined via the following formula: $(OD_{treated}-OD_{blank})/(OD_{control}-OD_{blank})\times100\%$.

The cytotoxicity of PASA/DOX and FASA/DOX at a carrier/DOX ratio of 10/1 (w/w) were compared to free DOX and Doxil at various DOX concentrations. FASA control was added to cells at concentrations equivalent to the amounts of carrier in the corresponding DOX formulations. In order to confirm folate-mediated active targeting, free folate (100 µM) was added along with the FASA/DOX micelles. Cells were incubated for 30 min in drug-containing medium and then cultured for another 48 h in fresh medium prior to MTT assay.

Tissue biodistribution. For in vivo tissue biodistribution study, 4T1.2 and CT26 tumor bearing mice (~300 mm³) were i.v. injected with free DOX, DOX-loaded PASA and FASA micelles (carrier/DOX weight ratio: 10/1), respectively. The mice were sacrificed and perfused at 24 h post injection. Tumors and major organs including heart, liver, spleen, lung and kidney were sectioned and observed under the fluorescence microscope (BZ-X710, Japan).

In vivo therapeutic study. In vivo antitumor efficacy of DOX-loaded PASA and FASA micelles was tested in syngeneic 4T1.2 mouse breast cancer model and CT26 mouse colon cancer model, respectively. Female BALB/c mice (4-6 weeks) were s.c. inoculated with 4T1.2 or CT26 cells ($5\times10^5$ cells per mouse). When the tumor volume reached ~50 mm³, mice were randomly divided into eight groups (n=5), and treated via tail vein injection with PBS, DOX, 5-ASA+DOX, Doxil, blank PASA micelles, blank FASA micelles, DOX-loaded PASA micelles or DOX-loaded FASA micelles, respectively once every three days for three times (polymer: 50 mg/kg, DOX: 5 mg/kg, 5-ASA: 20 mg/kg). Tumor sizes were monitored every three days following the initiation of the treatment and calculated by the formula: $(Length\times Width^2)/2$. Body weights were also followed as an indication of toxicity. After completion of the experiment, tumor and major organs were collected for hematoxylin and eosin (H&E) staining. Blood samples were collected for biochemical analysis of alanine transaminase (ALT) and aspartate aminotransferase (AST).

To evaluate the synergistic effects of anti-PD-1 and FASA/DOX, a syngeneic CT26 colon tumor model was established by inoculating $5\times10^5$ CT26 cells into the flank of BALB/c mice. When the tumor volume reached ~100 mm³, mice were randomly grouped (n=5), and treated with PBS, PD-1 antibody (BioCell), FASA/DOX and anti-PD-1+FASA/DOX, respectively, every three days for a total of three times (polymer: 25 mg/kg, DOX: 2.5 mg/kg, anti-PD-1: 5 mg/kg). FASA/DOX and anti-PD-1 treatment was administered i.v. or i.p., respectively. Tumor volumes were monitored every three days and calculated as described above. Body weights were also followed as an indication of systemic toxicity. After completing the in vivo experiment, tumor tissues and major organs were collected for histochemical staining. Blood sample were collected for ALT and AST analysis.

Quantification of tumor-infiltrating immune cells. BALB/c mice bearing CT26 tumors received various treatments via tail vein injection once every three days for three times. Tumors and spleens were harvested at 24 h after the last treatment. Single cell suspensions were prepared and stained for CD4, CD8, IFN-γ, Granzyme B, FoxP3 and macrophage (F4/80 and CD206) for flow cytometry analysis[20].

Histopathological Analysis. Tumors and major organs including heart, liver, spleen, lung and kidney were excised and fixed in PBS containing 10% formaldehyde after completion of the in vivo therapy study, followed by embedment in paraffin. The paraffin embedded samples were sectioned into slices at 4 µm using an HM 325 Rotary Microtome. The tissue slices were then subjected to H&E staining for histopathological examination under a Zeiss Axiostar plus Microscope (PA, USA).

ALT and AST assessment. Mouse serum was obtained for blood biochemical assessment. ALT and AST were measured by ALT/SGPT or AST/SGPT liqui-UV assay kit following manufacturer's protocols.

Prostaglandin E2 level analysis. To analyze the levels of prostaglandin E2 ($PGE_2$) production in different cell lines, the cell culture mediums were collected after overnight incubation. To test $PGE_2$ in the tumor tissues, the harvested tumors were homogenized, and the supernatants were obtained after centrifugation. $PGE_2$ in the supernatants was detected using Abcam Prostaglandin E2 ELISA Kit.

Statistical analysis. All values were presented as mean±standard error of mean (SEM). Statistical analysis was performed with two-tailed Student's t-test for comparison between two groups and one-way analysis of variance (ANOVA) for comparison between multiple groups. Results were considered statistically significant if p<0.05.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A polymer, comprising:
a hydrophobic polymer backbone,
a first plurality of pendant groups attached to the hydrophobic polymer backbone and comprising a moiety attached to the hydrophobic polymer backbone via a bond which is labile in vivo to release a first therapeutic compound which is a COX inhibitor, the moiety comprising a group to ionically interact with a second therapeutic compound, different from the first therapeutic compound, and
a second plurality of pendant groups attached to the hydrophobic polymer backbone and comprising at least one hydrophilic polymer.

2. The polymer of claim 1 wherein the hydrophobic polymer backbone is formed via radical polymerization of vinyl monomers.

3. The polymer of claim 2 wherein the hydrophobic polymer backbone is formed via a reversible-deactivation radical polymerization.

4. The polymer of claim 1 wherein the bond which is labile in vivo includes at least one of a reductive sensitive linkage, a pH-sensitive linkage, a ROS-sensitive linkage, a hypoxia-sensitive linkage, or a protease-sensitive linkage.

5. The polymer of claim 1 further comprising a third plurality of pendant groups attached to the hydrophobic polymer backbone and comprising at least one targeting group to target a region of interest in vivo.

6. The polymer of claim 5 wherein the at least one targeting group comprises a folate group, anisamide, peptide, or antibody.

7. The polymer of claim 5 wherein the at least one targeting group comprises a folate group.

8. The polymer claim 1 wherein the first therapeutic compound further includes a group capable of interacting via π-π bonding.

9. The polymer of claim 8 wherein the first therapeutic compound is 5-aminosalicylic acid, acedofenac, diclofenac, mefenamic acid, tolfenamic acid, sulfasalazine, balsalazide, olsalazine, or a derivative thereof which is active as a COX inhibitor.

10. The polymer of claim 8 wherein the first therapeutic compound is 5-aminosalicylic acid.

11. The polymer of claim 1 wherein a plurality of the polymers forms a micelle having a diameter less than 100 nm when combined with the second therapeutic compound.

12. The polymer of claim 1 wherein the second therapeutic compound includes an amino group to ionically interact with the group of the moiety.

13. The polymer of claim 1 wherein the second therapeutic compound further includes a group to interact via π-π bonding.

14. The polymer of claim 1 wherein the second therapeutic compound is an anticancer compound, an antiviral compound, an antibiotic compound, an antimycotic compound, an anti-rejection compound, an analgesic compound, an antioxidant compound, an immunomodulating compound, an antifungal compound, or an anti-inflammatory compound.

15. The polymer of claim 1 wherein the second therapeutic compound is doxorubicin, pirarubicin, aclarubicin, idarubicin, amrubicin, daunorubicin, epirubicin, cisplatin, nedaplatin, oxaliplatin, carboplatin, irinotecan, imatinib, lapatinib, dabrafenib, trametinib, alpelisib, osimertinib, sunitinib, ketoconazole, miconazole, fluconazole, olaparib, rucaparib, niraparib, talazoparib, veliparib, MK-2206 or a peptide.

16. The polymer of claim 1 wherein the first moiety is attached to the hydrophobic polymer backbone via a linker which interacts with the second therapeutic compound.

17. A formulation, comprising: a plurality of polymers comprising a hydrophobic polymer backbone, a first plurality of pendant groups attached to the hydrophobic polymer backbone and comprising a moiety attached to the hydrophobic polymer backbone via a bond which is labile in vivo to release as a first therapeutic compound which is a COX inhibitor and a second plurality of pendant groups attached to the hydrophobic polymer backbone and comprising at least one hydrophilic polymer and a second therapeutic compound, different from the first therapeutic compound, the moiety comprising a group to ionically interact with a group of the second therapeutic compound.

18. The formulation of claim 17 wherein each of the first therapeutic compound and the second therapeutic compound is a small molecule compound.

19. The formulation of claim 18 wherein each of the first therapeutic compound and the second therapeutic compound has a molecular weight below 1.5 kDa or 1 kDa.

20. The formulation of claim 17 wherein the hydrophobic polymer backbone is formed via radical polymerization of vinyl monomers.

21. The formulation of claim 20 wherein the hydrophobic polymer backbone is formed via a reversible-deactivation radical polymerization.

22. The formulation of claim 17 wherein the bond which is labile in vivo includes at least one of a reductive sensitive linkage, a pH-sensitive linkage, a ROS-sensitive linkage, a hypoxia-sensitive linkage, or a protease-sensitive linkage.

23. The formulation of claim 17 wherein the polymer further comprises a third plurality of pendant groups attached to the hydrophobic polymer backbone and comprising at least one targeting group to target a region of interest in vivo.

24. The formulation of claim 23 wherein the at least one targeting group comprises a folate group, anisamide, peptide, or antibody.

25. The formulation of claim 23 wherein the at least one targeting group comprises a folate group.

* * * * *